United States Patent
Tezuka et al.

(10) Patent No.: US 8,872,412 B2
(45) Date of Patent: Oct. 28, 2014

(54) ULTRASOUND TRANSDUCER, ULTRASOUND PROBE, AND A METHOD FOR MANUFACTURING ULTRASOUND TRANSDUCERS

(75) Inventors: Satoru Tezuka, Nasushiobara (JP); Yasuhisa Makita, Nasushiobara (JP); Yutaka Oonuki, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 337 days.

(21) Appl. No.: 13/070,257

(22) Filed: Mar. 23, 2011

(65) Prior Publication Data

US 2011/0248603 A1 Oct. 13, 2011

(30) Foreign Application Priority Data

Apr. 13, 2010 (JP) ................................ 2010-092542

(51) Int. Cl.
*B06B 1/06* (2006.01)
*H01L 41/047* (2006.01)
*A61B 8/00* (2006.01)

(52) U.S. Cl.
CPC ............. *B06B 1/0629* (2013.01); *A61B 8/4405* (2013.01); *A61B 8/4483* (2013.01); *G01K 11/004* (2013.01)
USPC ......................................... 310/334; 310/365

(58) Field of Classification Search
CPC ............................ B06B 1/0622; B06B 1/0629
USPC ................................. 310/322, 334, 335, 365
See application file for complete search history.

(56) References Cited

U.S. PATENT DOCUMENTS

| 4,217,684 A | 8/1980 | Brisken et al. |
| 5,267,211 A | 11/1993 | Miller et al. |
| 5,311,095 A | 5/1994 | Smith et al. |

(Continued)

FOREIGN PATENT DOCUMENTS

| CN | 1492999 A | 4/2004 |
| CN | 101011263 A | 8/2007 |

(Continued)

OTHER PUBLICATIONS

Combined Chinese Office Action and Search Report Issued Apr. 2, 2013 in Patent Application No. 201110091679.6 (with English translation of Categories of Cited Documents).

(Continued)

*Primary Examiner* — Derek Rosenau

(74) *Attorney, Agent, or Firm* — Oblon, Spivak, McClelland, Maier & Neustadt, L.L.P.

(57) ABSTRACT

An ultrasound transducer according to an embodiment has two-dimensionally arranged ultrasound vibrators. A wiring board block is a laminate of wiring boards which are arranged along the row direction in the arrangement. The wiring board has a first surface facing a rear surface of the ultrasound vibrators and a second surface on its opposite side. First connection parts are provided on the first surface corresponding to the arrangement, and are conducted with back electrodes of the vibrators. Second connection parts are provided on the second surface, and are provided corresponding to the first connection parts. Connecting leads establish conductivity between the first and second connection parts through a fourth surface which is perpendicular to the second and third surfaces. Electronic circuits are connected to the second surface of the wiring board block, and are conducted with the second connection parts.

10 Claims, 17 Drawing Sheets

(56) References Cited

U.S. PATENT DOCUMENTS

| | | | |
|---|---|---|---|
| 5,329,498 A * | 7/1994 | Greenstein | 367/155 |
| 6,102,860 A | 8/2000 | Mooney | |
| 6,308,389 B1 | 10/2001 | Tezuka | |
| 6,551,248 B2 | 4/2003 | Miller | |
| 6,625,856 B2 | 9/2003 | Tezuka | |
| 7,808,157 B2 * | 10/2010 | Oakley et al. | 310/334 |
| 2004/0024320 A1 | 2/2004 | Karasawa et al. | |
| 2005/0140248 A1 | 6/2005 | Kuniyasu et al. | |
| 2007/0145860 A1 | 6/2007 | Aoki et al. | |
| 2007/0244392 A1 * | 10/2007 | Tezuka | 600/459 |
| 2008/0200812 A1 | 8/2008 | Osawa | |
| 2009/0058228 A1 | 3/2009 | Wakabayashi et al. | |
| 2009/0262605 A1 | 10/2009 | Wakabayashi et al. | |

FOREIGN PATENT DOCUMENTS

| | | |
|---|---|---|
| CN | 101378605 A | 3/2009 |
| CN | 101559420 A | 10/2009 |
| JP | 2000-166923 | 6/2000 |
| JP | 2001-292496 | 10/2001 |
| JP | 2005-277864 | 10/2005 |
| JP | 2006-122105 | 5/2006 |
| JP | 2007-515268 | 6/2007 |
| JP | 2008-200300 | 9/2008 |
| WO | WO 2005/053863 A1 | 6/2005 |

OTHER PUBLICATIONS

Office Action issued Nov. 12, 2013, in Japanese Patent Application No. 2010-092542.

* cited by examiner

ULTRASOUND TRANSDUCER, ULTRASOUND PROBE, AND A METHOD FOR MANUFACTURING ULTRASOUND TRANSDUCERS

CROSS-REFERENCE TO RELATED APPLICATION

This application is based upon and claims the benefit of priority from Japanese Patent Application No. 2010-92542 filed Apr. 13, 2010; the entire contents of which are incorporated herein by reference.

FIELD

The present embodiment relates to an ultrasound probe, an ultrasound transducer and a method for manufacturing ultrasound transducers.

BACKGROUND

For image generation using an ultrasound imaging apparatus, ultrasound probes are used. In recent years, for ultrasound probes, 2D array ultrasound transducers have been used. For the 2D array ultrasound transducers, the number of elements of piezoelectric transducers is substantially large. Therefore, wiring of connecting leads that connect elements (ultrasound transducers) to electronic circuits (delay circuit, etc.) causes a problem. That is, when the number of leads that are connected to the elements arranged two-dimensionally is substantially large (for example, 4096), while the overall size of an ultrasound transducer is small, it is difficult to ensure that there is space to establish wiring of the leads.

It is necessary to solve this type of wiring problem pertaining to connecting leads. In order to solve this problem, processing that adds signals from piezoelectric transducers by, for example, an electric circuit etc. is performed. By performing such processing, the number of leads that are wired between the piezoelectric transducers and the electronic circuits (delay circuit, etc.). Furthermore, arrangement of this circuit is also a problem. That is, because the further the distance between the piezoelectric transducers and the electronic circuits is, the longer the length of the leads is, not only the arrangement of the leads becomes difficult, but problems of cross talk or noise arise. These problems are desired to be solved.

For example, conventionally, an ultrasound transducer with the configuration in which integrated circuits (IC's) are disposed on surfaces in the opposite direction to the direction of ultrasonic radiation, and piezoelectric transducers and IC's are directly electrically connected is proposed (for example, U.S. Pat. No. 6,551,248). By applying this configuration, the problems of arrangement of wiring caused by the length of leads, and the problems of cross talk and noise can be solved. Meanwhile, in the explanation below, the surface of a piezoelectric transducer in the opposite direction to the direction of ultrasonic radiation may be described as the "rear surface".

Moreover, conventionally, depending on a body region, ultrasound probes in various shapes have been used. When diagnosing the circulatory system, such as the heart, using an ultrasound imaging apparatus, an ultrasound probe is applied from the gap between the ribs. The ultrasound probe that is used in these cases is generally configured such that it has an ultrasound transducer in which the aperture of the ultrasonic radiation surface is small and in which the ultrasonic radiation surface is flat.

Moreover, in contrast, when diagnosing the digestive system, such as the liver, using the ultrasound imaging apparatus, the distance between the target diagnostic section and the body surface in subjects is relatively long. Moreover, when diagnosing the digestive system, the area of the target diagnostic section in subjects is relatively wide.

Furthermore, when diagnosing the diagnostic system, it is also necessary to discharge the gas inside the body of subjects, which adversely affects the ultrasonography in the ultrasonographic field.

The ultrasound probe that is used in these cases is generally configured such that it has an ultrasound transducer in which the aperture of the ultrasonic radiation surface is large and the ultrasonic radiation surface is formed in a curved shape having an arc shape, or a convex shape.

For the purpose of enlarging the aperture of the ultrasonic radiation surface of the ultrasound probe, it is difficult to make the respective size of the piezoelectric transducer in the ultrasound transducer large. That is, if the size of the piezoelectric transducer in the ultrasound transducer is made large, it may decrease the resolution capability; hence, there is a limitation on making the size of the piezoelectric transducer large. Therefore, when using an ultrasound probe having a large aperture, in order to make the ultrasonic radiation surface large, it is necessary to increase the number of piezoelectric transducers. However, that number is substantially large.

In an ultrasound probe, when the aperture of the ultrasonic radiation surface is large and when the ultrasonic radiation surface has a curved shape having an arc shape, or a convex shape, it is not easy to make the size of the IC's of the ultrasound transducer large, and moreover, the manufacturing cost is increased.

Therefore, when the aperture of the ultrasonic radiation surface is large and when the ultrasonic radiation surface has a curved shape having an arc shape, or a convex shape, it is difficult to dispose the IC's on the rear surface of the piezoelectric transducer as shown in U.S. Pat. No. 6,551,248. That is, it is not easy to dispose the IC's corresponding to the rear surface of the convex shaped or curve-shaped group of piezoelectric transducers in a high-density and space-saving manner.

Moreover, it is not easy to form the IC's having a shape corresponding to the rear surface of the convex shaped or curve-shaped group of piezoelectric transducers. Moreover, even if it is possible to provide or form these types of IC's, the manufacturing cost increases.

As described above, conventionally, depending on the number of the piezoelectric transducers or the arrangement pattern of the piezoelectric transducer, there have been various limitations and there have been cases in which it was difficult to set the IC's.

DETAILED DESCRIPTION

Figure 1:
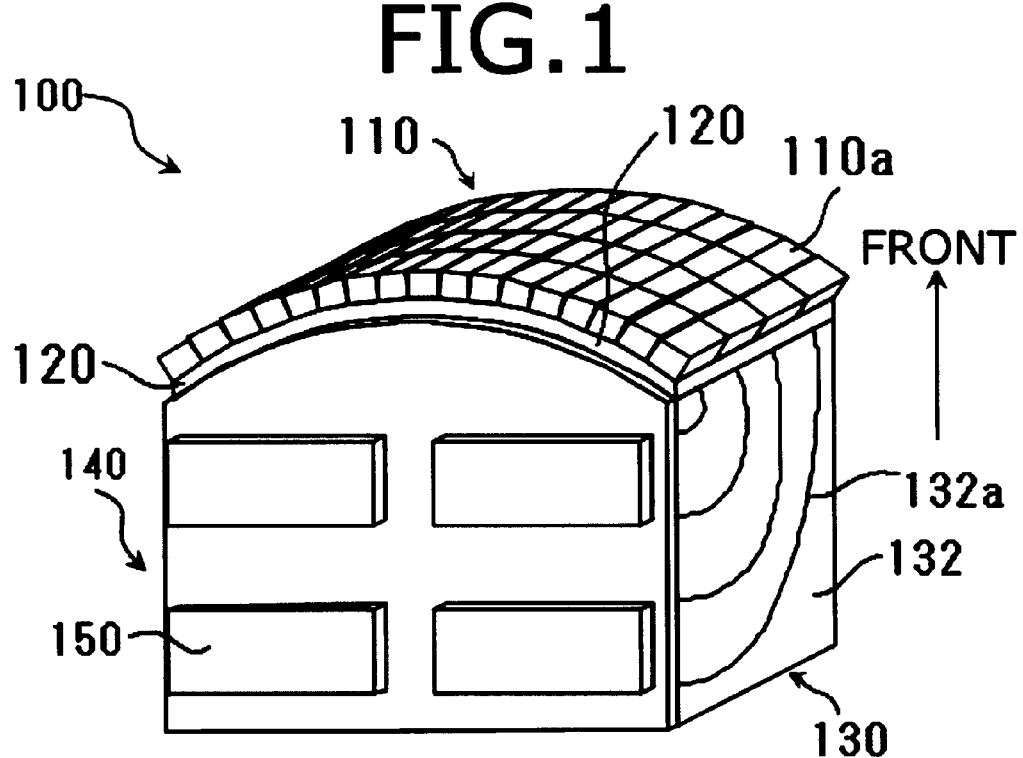
FIG. 1 is a schematic perspective view showing an ultrasound transducer according to the first embodiment.

Embodiments are intended to provide technology that can easily connect channels and electronic circuits, regardless of the area of an ultrasonic radiation surface and an arrangement pattern.

An ultrasound transducer according to an embodiment comprises a group of ultrasound vibrators, a wiring board block, first connection parts, second connection parts, connecting leads and electronic circuits. The group of ultrasound vibrators is composed of two-dimensionally arranged ultrasound vibrators. Each of the ultrasound vibrators includes a piezoelectric transducer. A front electrode is formed on a front surface of the piezoelectric transducer. The front surface is the ultrasonic radiation surface. A back electrode is formed on the rear surface of the piezoelectric transducer. The wiring board block is composed of a laminate of a plurality of wiring boards. These wiring boards are arranged along the row direction or the column direction with respect to the two-dimensional arrangement. Each of the wiring boards has a first surface facing the rear surface of the ultrasound vibrators and a second surface on the opposite side of the first surface. The first connection parts are provided on the first surface corresponding to the arrangement of the ultrasound vibrators.

The first connection parts are conducted with the back electrodes. The second connection parts are provided on the second surface or a third surface. The third surface is perpendicular to the second surface. The second connection parts are provided corresponding to the first connection parts respectively. The connecting leads are configured to establish conductivity between the first connection parts and the second connection parts through a fourth surface. The fourth surface is perpendicular to both the second surface and the third surface of the wiring boards. The electronic circuits are connected to a surface of the wiring board block on which the second connection parts are provided. The electronic circuits are conducted with the second connection parts. The electronic circuits process signals from the piezoelectric transducers.

An ultrasound probe according to an embodiment comprises the ultrasound transducer above and an interface part. The interface part is configured to establish conductivity between an external device and the electronic circuits.

According to an embodiment, an ultrasound probe having a group of ultrasound vibrators and wiring boards is manufactured with the following processes. Here, the group of ultrasound vibrators is composed of two-dimensionally arranged ultrasound vibrators. Each of the ultrasound vibrators includes a piezoelectric transducer in which a front electrode is formed on the front surface (that is, the ultrasonic radiation surface), and in which a back electrode is formed on the rear surface. Each of the wiring boards has a first surface facing the rear surface, a second surface on the opposite side thereof, and a third surface that is perpendicular to the second surface. The method for manufacturing this ultrasound probe comprises: a process of providing first connection parts on said first surface corresponding to the arrangement of said ultrasound vibrators, providing second connection parts on said second surface corresponding to said first connections respectively, and providing connecting leads that establish conductivity between said first connection parts and said second connection parts on a fourth surface that is perpendicular to said second surface and said third surface; a process of forming a wiring board block by laminating a plurality of said wiring boards along a first direction with respect to said two-dimensional arrangement or a second direction that is perpendicular to said first direction; and a process of establishing conductivity between said first connection parts and said back electrodes by directly or indirectly connecting said first surface to said rear surface of said ultrasound vibrator.

Below, the ultrasound transducer, the ultrasound probe and the method for manufacturing an ultrasound probe according to embodiments are described with reference to FIG. 1 to FIG. 16B.

[First Embodiment]

(Schematic Configuration of the Ultrasound Transducer)

Figure 2:
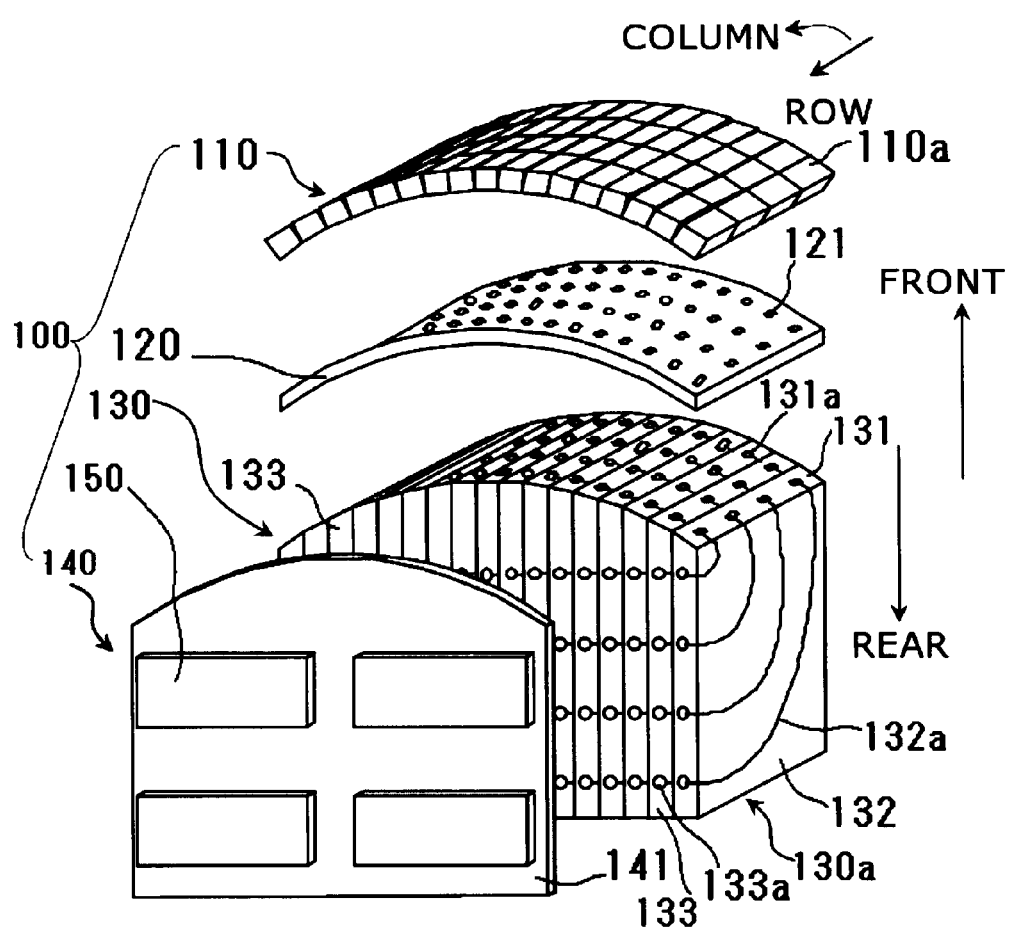
FIG. 2 is a schematic deal perspective view showing the ultrasound transducer according to the first embodiment.
Figure 3:
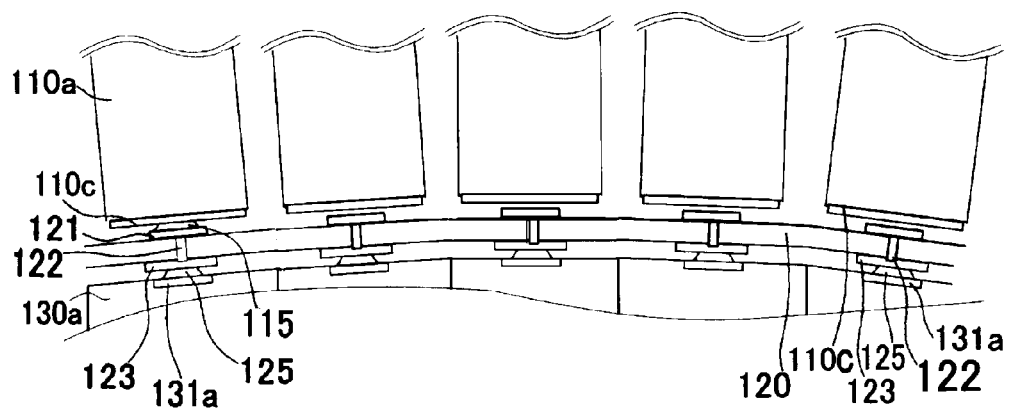
FIG. 3 is, in the ultrasound transducer according to the first embodiment, a schematic cross-sectional view showing a connection state of ultrasound vibrators and wiring boards that are mediated by a flexible circuit board.

With reference to FIG. 1 to FIG. 5, an ultrasound transducer 100 according to the first embodiment is described. FIG. 1 is a schematic perspective view showing the ultrasound transducer 100. Moreover, FIG. 2 is a schematic deal perspective view showing the ultrasound transducer 100. FIG. 3 is, in the ultrasound transducer 100, a schematic cross-sectional view showing the connection state of ultrasound vibrators 110a and wiring boards 130a that are mediated by a flexible circuit board 120. The schematic configuration of the ultrasound transducer 100 according to the present embodiment is described below. Moreover, the number of the ultrasound vibrators 110a in an arrangement and the number of the wiring boards 130a in the ultrasound transducer 100 shown in each figure are shown for conceptual purposes. Moreover, the shape that is constituted by the entire arrangement of the ultrasound transducer 100 shown in each figure is also one example, and it is also possible to have other configuration.

As shown in FIG. 1, the ultrasound transducer 100 according to the embodiment has a group of ultrasound vibrators 110 that is constituted by two-dimensionally arranging the ultrasound vibrators 110a. The group of ultrasound vibrators 110 in FIG. 2 has a two-dimensional arrangement constituting of a row direction and a column direction. With regard to the arrangement of the ultrasound vibrators 110a in this group of ultrasound vibrators 110, for example, in order to make it suitable to diagnose the digestive system, it is possible to configure such that the diameter of the entire shape of the ultrasonic radiation surface is made so as to be large and the ultrasonic radiation surface has a convex shape or an arc shape. As shown in FIG. 1, the ultrasound transducer 100 having the group of ultrasound vibrators 110 with a convex surface or curved surface can also be applied to the cases in which the distance from the body surface to the target diagnostic section is relatively long. Moreover, with the ultrasound transducer 100 having the large aperture, the area of the target diagnostic section is also widened. Furthermore, this type of the ultrasound transducer 100 can discharge the gas inside the body that adversely affects the ultrasonography from the ultrasonographic field.

As shown in FIG. 1 and FIG. 2, on the rear surface of the group of ultrasound vibrators 110, a flexible circuit board 120 is disposed adjacently. Here, the "rear surface" refers to the surface that is on the side of the opposite direction from the radiation direction of the ultrasound with respect to the group of ultrasound vibrators 110.

Moreover, the radiation direction of the ultrasound with respect to the ultrasound transducer 100 may be hereinafter simply described as a "front". Similarly, the direction opposite from the "front" may be simply described as a "rear". Moreover, the surface on the opposite side from the rear surface of the group of ultrasound vibrators 110 may be hereinafter simply described as a "front surface". Moreover, hereinafter, when describing the ultrasound vibrators 110a, their surfaces may be simply described as the "front surface" and the "rear surface" corresponding to the "front surface" and "rear surface" of the group of ultrasound vibrators 110.

Moreover, as shown in FIG. 2, on the rear side of the flexible circuit board 120, a wiring board block (a group of wiring boards) 130 is disposed. The wiring board block 130 is constituted by arranging the plurality of wiring boards 130a. Each of the wiring boards 130a is formed in a thick-plate shape. Moreover, the wiring board block 130 having 5 flat surfaces and 1 convex surface (or a curved surface), for example, as shown in FIG. 2 is formed by combining the plurality of wiring boards 130a. Moreover, the surface on the front side of this wiring board block 130 may be hereinafter simply described as the "front surface" or "front surface 131", and the surface on the opposite side from the front 131 may be described as the "rear surface". The front surface of the wiring board 130a and the front surface of the wiring board block 130 are one example of a "first surface", and their rear surfaces are one example of a "second surface". Moreover, the thickness of these wiring boards 130a, for example, can be made so as to be the same as the arrangement interval in a 2D array of the ultrasound vibrators 110a.

Moreover, on the side surface of the wiring board block 130, an electronic circuit board 140 is provided. That is, by combining the plurality of wiring boards 130a, to the wiring board block 130, the side surfaces 133 of the combined wiring boards 130a are strung out to form a group of substantially flat side surfaces. For this group of side surfaces, the electronic circuit board 140 is provided. To this electronic circuit board 140, electronic circuits 150 are provided.

Moreover, the electronic circuits 150 are provided on the surface 141 of the electronic circuit board 140. The surface 141 is the surface of the electronic circuit board 140 on the opposite side from the surface of the wiring board block 130 side.

On each of the rear surfaces of the ultrasound vibrators 110a in the group of ultrasound vibrators 110, electrodes are provided.

Moreover, as shown in FIG. 2, on the rear surface of the group of ultrasound vibrators 110, the flexible circuit board 120 is disposed. On the surface on the front side of the flexible circuit board 120, a plurality of third connection pads 121 are provided. The electrodes on the rear surface of the ultrasound vibrators 110a establish conductivity with the third connection pads 121. Moreover, on the flexible circuit board 120, penetrating electrodes 120 (refer to FIG. 3) are provided.

Moreover, on the rear surface of the flexible circuit board 120, fourth connection pads 123 (refer to FIG. 3) are provided. The third connection pads 121 establish conductivity with the fourth connection pads 123 through the penetrating electrodes 122.

Figure 4:
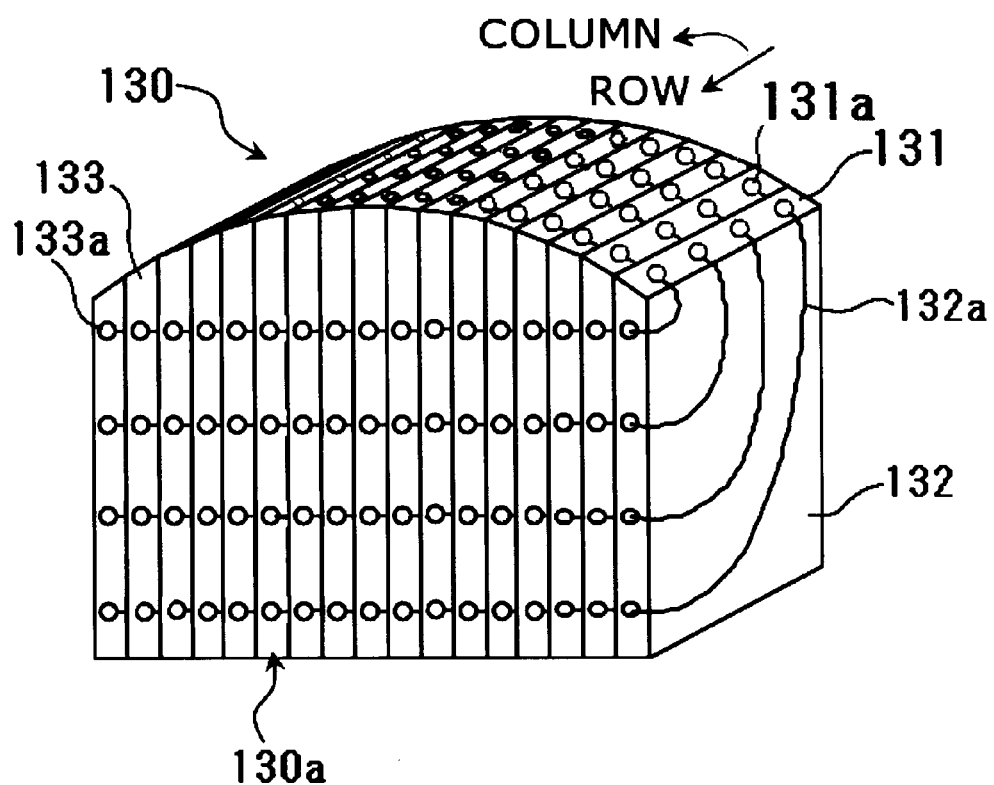
FIG. 4 is a schematic perspective view showing a wiring board block of the ultrasound transducer according to the first embodiment.

As shown in FIG. 2 and FIG. 4, on the front surface 131 of the respective wiring boards 130a in the wiring board block 130, a plurality of first connection pads 131a are provided adjacent to each other. Moreover, as shown in FIG. 2 and FIG. 3, each of the first connection pads 131a is connected to the fourth connection pads 123 that are disposed on the rear surface of the flexible circuit board 120.

Moreover, to these first connection pads 131a, connecting leads 132a are connected. Furthermore, the connecting leads 132a are connected to second connection pads 133a by passing through a second board surface 132 of the respective wiring boards 130a from the first connection pads 131a. Therefore, the first connection pads 131a and the second connection pads 133a are connected to each other through the connecting leads 132a. Moreover, the connecting leads 132a can be, for example, configured as a wiring pattern that is printed on the wiring board block 130.

Moreover, the first connection pads 131a according to the present embodiment are one example of "first connection parts".

Moreover, the second connection pads 133a according to the present embodiment are one example of "second connection parts".

Moreover, the third connection pads 121 are one example of "third connection parts". Moreover, the fourth connection pads 123 are one example of "fourth connection parts".

(Configuration of the Ultrasound Vibrators)

Next, with reference to FIG. 3, the ultrasound vibrators 110a of the ultrasound transducer 100 of the present embodiment are described.

Moreover, the basic configuration of the ultrasound vibrators 110a is described with omitting the figures. The ultrasound vibrator 110a is configured by comprising, in the radiation direction of the ultrasound, sequentially, a backing material, a back electrode, a piezoelectric transducer, a front electrode, and acoustic matching layers. On the front surface of the piezoelectric transducer, the front electrode is provided, and furthermore, on the front side of the front electrode, acoustic matching layers are provided. Moreover, on the rear surface of the piezoelectric transducer, the back electrode is provided, and furthermore, on the rear side of the back electrode, the backing material is provided. Moreover, an electric lead connects the electrode of the piezoelectric transducer to the rear surface of the ultrasound vibrator 110a. On the rear surface of the ultrasound vibrator 110a, a terminal 110c (connection pad) is provided. The tip of the electric lead is connected to the terminal 110c (refer to FIG. 3).

Moreover, as shown in FIG. 1, when the ultrasonic radiation surface of the ultrasound transducer 100 is curved, as an example, the ultrasound vibrators 110a are disposed by sloping in a specified angle with respect to the adjacent ultrasound vibrators 110a. Moreover, as another example, it is also possible to use the configuration in which the ultrasound vibrators 110a are disposed in predefined numbers only (for example 2 elements) in parallel to each other (this cluster is referred to as one block), and these block of the ultrasound vibrators are disposed by sloping in a specified angle with respect to the adjacent blocks.

Based on the signals transmitted from an ultrasound imaging apparatus body 500, a voltage is applied to the piezoelectric transducers through the electronic circuits 150, the connecting leads 132a, the front electrodes, the back electrodes, etc., of the ultrasound transducer 100. Each of the piezoelectric transducers in the ultrasound vibrators 110a converts the applied electric signals to the ultrasonic pulse. The ultrasonic pulse that is radiated from the piezoelectric transducer is transmitted to a subject through the acoustic matching layers an acoustic lens. Subsequently, when the ultrasound vibrators 110a receive the reflected waves from the subject, the reflected waves are converted to the electric signals. Each of the electric signals is transmitted to the corresponding electronic circuits 150 after passing through the flexible circuit board 120, the first connection pads 131a of the wiring board block 130, the connecting leads 132a, the second connection pads 133a, and the electronic circuit board 140.

Furthermore, each of the electric signals is transmitted to the ultrasound imaging apparatus body 500, for example, after an addition processing is applied and the number of channels is reduced by the electronic circuits 150. The details are described below.

<Piezoelectric Transducer>

As the piezoelectric transducer in the ultrasound vibrators 110a, it is possible to use PZT (lead zirconate titanate)/Pb(Zr, Ti)O3), barium titanate (BaTiO3), a single crystal of PZNT (lead zinc niobate titanate)/Pb(Zn1/3Nb2/3)O3-PbTiO3), and a single crystal of PMNT (lead magnesium niobate titanate)/Pb (Mg1/3Nb2/3) O3-PbTiO3).

<Backing Material>

The backing material absorbs the ultrasound that is emitted on the other side from the radiation direction of the ultrasound and suppresses the excessive vibration of each piezoelectric transducer. As the backing material, any materials can be used from a perspective of acoustic attenuation, acoustic impedance, etc. As the backing material, there are, for example, epoxy resins such as PZT powder or tungsten powder, rubber filled with polyvinyl chloride or ferrite powder, or a porous ceramic soaked with resin such epoxy.

<Acoustic Matching Layers>

Acoustic matching layers in the ultrasound vibrators 110a adjust the acoustic impedance between the piezoelectric transducers and the subject. For this acoustic adjustment, those made of resin materials such as epoxy resin can be used. Moreover, the acoustic matching layers can be made so as to have one layer or they can be made so as to have two layers or more.

(Configuration Between Ultrasound Vibrators, Flexible Circuit Board, and Wiring Boards)

Next, a connection configuration of the ultrasound vibrators 110a and the flexible circuit board 120 in the ultrasound transducer 100 according to the present embodiment is described with reference to FIG. 1 to FIG. 3. Moreover, a connection configuration of the flexible circuit board 120 and the wiring board 130a in the ultrasound transducer 100 is described.

As shown in FIG. 2, the flexible circuit board 120 is disposed adjacent to the rear side with respect to the group of ultrasound vibrators 110. On the front surface of the flexible circuit board 120, the third connection pads 121 are provided.

That is, in the adjacent region between the ultrasound vibrators 110a and the flexible circuit board 120, the terminals 110c of the ultrasound vibrators 110a and the third connection pads 121 of the flexible circuit board 120 are disposed. Furthermore, as shown in FIG. 3, these terminals 110c and the third connection pads 121 are connected by attachment parts 115 having conductivity. With these attachment parts 115, the terminals 110c and the third connection pads 121 establish conductivity with each other. Furthermore, the third connection pads 121 and the electrodes of the piezoelectric transducers are conducted with each other through the terminals 110c.

Moreover, as shown in FIG. 3, the third connection pads 121 on the front surface of the flexible circuit board 120 are conducted with the fourth connection pads 123 on the rear surface of the flexible circuit board 120 through the penetrating electrodes (electrode holes) 122. For example, the penetrating electrodes 122 are configured as through holes that are provided by penetrating the flexible circuit board 120 or via holes etc. In this example, the penetrating electrodes 122 are provided by penetrating the inner section of the flexible circuit board 120. Moreover, on the front surface side of the flexible circuit board 120, they are connected to the third connection pads 121.

Moreover, the penetrating electrodes 122 are connected to the fourth connection pads 123 on the tip on the opposite side from the third connection pads 121. In this way, conductivity is established between the front surface and the rear surface of the flexible circuit board 120. Moreover, in FIG. 3, the arrangement interval of the third connection pads 121 and the arrangement interval of the fourth connection pads 123 have the same distance. However, it is possible to make the arrangement interval of the fourth connection pads 123 wider than the arrangement interval of the third connection pads 121. For example, with the penetrating electrodes 122 of the flexible circuit board 120, it is possible to make the arrangement interval of the fourth connection pads 123 wider than the arrangement interval of the third connection pads 121.

Moreover, as shown in FIG. 2, on the rear side of the flexible circuit board 120, the wiring board block 130 is disposed adjacently.

Moreover, the wiring board block 130 is formed by bundling up the plurality of wiring boards 130a. In this way, by stringing up the front surfaces 131 of the wiring boards 130a, a group of the front surface 131 is formed. The front surface group of the wiring boards 130a is the front surface of the wiring board block 130. In the adjacent region between the front surface of the wiring board block 130 and the rear surface of the flexible circuit board 120, as shown in FIG. 3, the first connection pads 131a of the wiring boards 130a and the fourth connection pads 123 of the flexible circuit board 120 are disposed.

That is, on the surface 131 of the respective wiring boards 130a, according to the arrangement and the position of the fourth connection pads 123 that are provided on the rear surface of the flexible circuit board 120, the first connection pads 131a are provided adjacent to each other. Moreover, as shown in FIG. 3, these first connection pads 131a and the fourth connection pads 123 are connected to by the attachment parts 125. With the attachment parts 125, the first connection pads 131a and the fourth connection pads 123 establish conductivity with each other. As a result, through the fourth connection pads 123, the third connection pads 121, and the terminals 110c, the first connection pads 131a and the electrodes of the piezoelectric transducers are conducted to one another. That is, the ultrasound vibrators 110a and the wiring board block 130 are electrically connected through the flexible circuit board 120.

Moreover, the flexible circuit board 120 is bent in accordance with the shape and undulation of the rear surface of the group of ultrasound vibrators 110. Furthermore, the flexible circuit board 120 is bent in accordance with the shape and undulation of the front surface of the wiring board block 130. Based on these configurations, connecting the terminals 110c to the third connection pads 121 and connecting the fourth connection pads 123 to the first connection pads 131a are easily performed As a result, connecting the terminals 110c to the first connection pads 131a is also easily performed. However, depending on the shape of the rear surface of the group of ultrasound vibrators 110 and the shape of the front surface 131 of the wiring board block 130, there are cases in which connecting the first connection pads 131a to the terminals 110c is originally not difficult.

In those cases, without providing the flexible circuit board 120, it is possible to directly connect the group of ultrasound vibrators 110 to the wiring board block 130.

(Configuration of the Wiring Boards and the Wiring Board Block)

Next, with reference to FIG. 1, FIG. 2, FIG. 4, and FIG. 5, the wiring boards 130a and the wiring board block 130 in the ultrasound transducer 100 are described. FIG. 4 is a schematic perspective view showing the wiring board block 130 of the ultrasound transducer 100.

Figure 5:
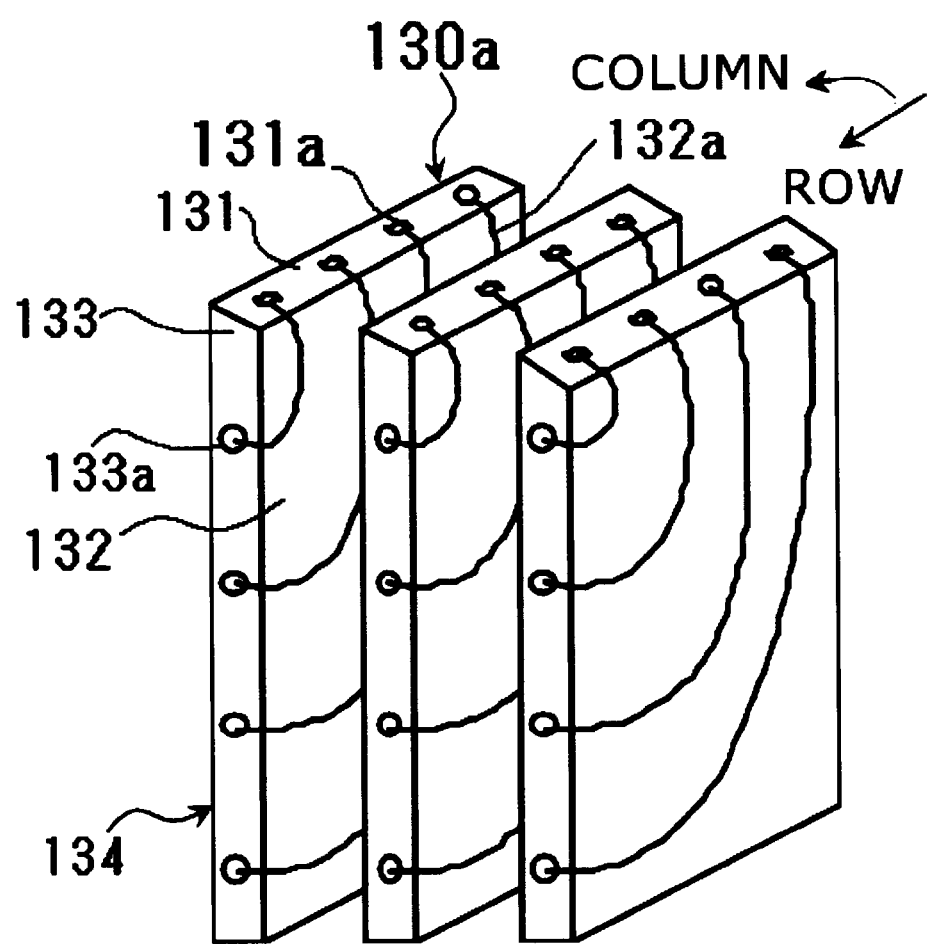
FIG. 5 is a schematic perspective view showing the wiring boards of the ultrasound transducer according to the first embodiment.

FIG. 5 is a schematic cross-sectional view showing the wiring boards 130a of the ultrasound transducer 100. Moreover, the number of the first connection pads 131a and the number of the wiring boards 130a are for conceptual purposes, and they differ from the actual ones.

Moreover, the number of rows and the number of columns of the first connection pads 131a that are provided depending on the terminals 110c are also one example, and it is possible to have another configuration.

The wiring board block 130 comprises the electronic circuits 150 and the electronic circuit board 140. The electronic circuits 150 process the signals that are transmitted to and received from the group of ultrasound vibrators 110. The electronic circuit board 140 connects the electronic circuits 150 to the wiring board block 130. That is, the wiring board block 130 establishes the wiring between the respective ultrasound vibrators 110a and the electronic circuits 150. As shown in FIG. 4, the plurality of wiring boards 130a are disposed and combined by placing them adjacent to each other in order to form an aggregation of the wiring boards 130a. The aggregation of the wiring boards 130a is the wiring board block 130. Moreover, as shown in FIG. 5, the wiring boards 130a are arranged with the surface on which the first connection pads 131a are provided (front surface 131) facing the same direction.

The arrangement direction of the wiring boards 130a, for example, corresponds to the arrangement direction of the ultrasound vibrators 110a. Moreover, the front surface 131 is sloped or curved.

Due to the arrangement of the wiring boards 130a, the sloped or curved surface of the wiring boards 130a is integrated into one string in order to form a curved surface or convex surface of the wiring board block 130. Moreover, the wiring boards 130a are, as described later, made so as to be sloped or curved according to the arrangement of the ultrasound vibrators 110a.

<Wiring boards>

As shown in FIG. 5, each of the wiring boards 130a is formed in a thick-plate shape containing a first board surface 134, a second board surface 132, a side surface 133, a front surface 131, and the rear surface. The first board surface 134 and the second board surface 132 on the opposite side from the first board surface 134 are the widest surface in the wiring board 130a. Moreover, the side surface 133 and the side surface (not shown in the figures) on the opposite side from the side surface 133 are substantially perpendicular to the first board surface 134 and the second board surface 132. Moreover, in the wiring board 130a, the rear surface (not shown in the figures) is perpendicular to the first board surface 134 and the side surface 133. The surface that is on the opposite side of the rear surface of the wiring board 130a is the front surface 131. The front surface 131 is the curved surface or the sloped surface.

Moreover, as the wiring boards 130a, those in which the shape accuracy can be assured, such as aluminum, hard resin, and ceramic are used.

Moreover, for each of the wiring boards 130a, the length from the rear surface in the direction toward the front surface 131 is longer than the length from the side surface 133 to the side surface on the opposite side. Moreover, hereinafter, for ease of explanation, the length from the rear surface in the direction toward the front surface 131 of the wiring boards 130a is described as the "height", and the length from the side surface 133 to the side surface on the opposite side is described as the "width".

Moreover, as shown in FIG. 4, the height of the wiring boards 130a is not uniform. The wiring board 130a that is positioned in the middle of the arrangement is formed so as to be the highest. Moreover, as shown in FIG. 4, as it faces toward both ends of the arrangement from the middle, the height of the wiring boards 130a is shortened. By combining these wiring boards 130a by placing them adjacent to each other, the front surfaces 131 of the wiring boards 130a are strung up, and the curved surface or the convex surface is formed. Moreover, as shown in FIG. 4, by gradually changing the height of the wiring boards 130a and by arranging the wiring boards 130a such that the edges of the adjacent front surfaces 131 are strung up, the curved surface of the wiring board block 130 having less unevenness is formed.

Moreover, the front surface of the wiring board block 130 is formed according to the shape on the rear surface side of the group of ultrasound vibrators 110. The front surface of the wiring board block 130a is constituted by an aggregation of the front surface 131 of the wiring boards 130a. That is, the aggregation of the front surface 131 of the wiring boards 130a is formed according to the shape on the rear surface side of the group of ultrasound vibrators 110. Moreover, when the rear surface of the group of ultrasound vibrators 110 is not curved, for example, when the ultrasound vibrators 110a are arranged in a stair shape, the front surface of the wiring board block 130 is also formed in a stair shape according to the shape of the rear surface of the group of ultrasound vibrators 110. At this time, for the adjacent wiring boards 130a, the heights of the edges of the second board surfaces 132 and the heights of the edges of the first board surfaces 134 are made to be different.

<First Connection Pads>

Moreover, as shown in FIG. 4 and FIG. 5, on the front surface of the wiring boards 130a, the first connection pads 131a are provided with a predefined arrangement interval. The arrangement interval of these first connection pads 131a, for example, has the same as the arrangement interval of the ultrasound vibrators 110a. However, the arrangement interval of the first connection pads 131a may be wider than the arrangement interval of the ultrasound vibrators 110a. For example, this can be achieved by making the arrangement interval of the fourth connection pads 123 so as to be wider than the arrangement interval of the third connection pads 121 in flexible circuit board 120.

In these cases, the arrangement interval of the first connection pads 131a has the same interval as the fourth connection pads 123.

Moreover, although the first connection pads 131a, which are shown in the figures, are arranged in one row in the middle of the front surface 131, it is not limited to this configuration. For example, depending on the thickness of the wiring boards 130a, it is possible to arrange the first connection pads 131a in a plurality of rows on the front surface 131. Moreover, rather than in the middle of the front surface 131, it is possible to arrange the first connection pads 131a in the marginal region of the front surface 131.

<Connecting Leads>

Moreover, as shown in FIG. 2, FIG. 4, and FIG. 5, connecting leads 132a are connected to the first connection pads 131a on the front surface 131. Furthermore, the connecting leads 132a are connected to the second connection pads 133a on the side surface 133. For example, the connecting leads 132a are, as shown in FIG. 5, connected to the second connection pads 133a by passing through the second board surface 132 from the front surface 131. Moreover, the disposition interval of the connecting leads 132a in the second board surface 132, for example, as shown in FIG. 5, is the same as the disposition interval of the first connection pads 131a up to the middle of the second board surface 132. Subsequently, the connecting leads 132a are disposed by widening the interval according to the disposition interval of the second connection pads 133a.

<Second Connection Pad>

Moreover, as shown in FIG. 4 and FIG. 5, on the side surface 133 of the wiring boards 130a, the second connection pads 133a are provided with a predefined arrangement interval. The arrangement interval of the second connection pads 133a, as shown in FIG. 5 as one example, can be widened with respect to the interval of the first connection pads 131a. This is because, for each of the wiring boards 130a, if the side surface 133 is formed so as to be longer than the front surface 131, the layout area of the second connection pads 133a is widened. Moreover, it is not necessary for the disposition interval of the second connection pads 133a to be constant, and for example, it is possible to have a configuration in which the second connection pads 133a are unevenly distributed on the front side or the rear side.

Moreover, it is also possible to have a configuration in which groups of the second connection pads 133a are disposed with wider interval. Moreover, it is possible to dispose the second connection pads 133a according to the configuration of the connection pads of the electronic circuit board 140. Moreover, rather than the middle of the side surface 133, it is also possible to unevenly arrange the second connection pads 133a toward the marginal region of the side surface 133. Moreover, for the side surface 133, it is also possible to arrange the second connection pads 133a in a plurality of rows, as is the case with the first connection pads 131a.

As described above, with regard to the ultrasound transducer 100 according to the present embodiment, the first connection pads 131a are provided on the front surface 131 of the generally thick-plate shaped wiring boards 130a. Moreover, to the first connection pads 131a, the connecting leads 132a are connected. The connecting leads 132a are made so as to pass through the second board surface 132 from the front surface 131 and reach the side surface 133. Moreover, the connecting leads 132a are connected to the second connection pad 133a on the side surface 133.

Furthermore, the wiring boards 130a are arranged and combined such that the side surface 133 is strung up in one string. By aggregating and stringing up the side surfaces 133, a substantially flat surface is formed on the side surface of the wiring board block 130. On the side surface of the wiring board block 130, the electronic circuit board 140 and the electronic circuits 150 are disposed. Moreover, when the rear surface of the group of ultrasound vibrators 110 is curved shaped or convex shaped, the front surface of the wiring board block 130 is formed corresponding to the shape of the rear surface of the group of ultrasound vibrators 110. Furthermore, each of the first connection pads 131a are conducted with the ultrasound vibrators 110a.

The electronic circuits 150 are disposed on the substantially flat-shaped side surface side of the wiring board block 130. That is, the electronic circuits 150 are electrically connected to the second connection pads 133a that are provided on the side surface. Moreover, as described above, to the second connection pads 133a, the connecting leads 132a that are pulled out from the wiring boards 130a are connected.

Therefore, by disposing the electronic circuits 150 on the side surface of the wiring board block 130, the electronic circuits 150 is conducted with each of the ultrasound vibrators 110a. As a result, because electronic circuits for the ultrasound transducer according to the arrangement pattern of the ultrasound vibrators 110a or the large-sized electronic circuits, etc., are not required, it becomes possible to obtain the 2D array ultrasound transducer with a simple manufacturing process.

(Configuration of the Electronic Circuit Board and the Electronic Circuits)

Next, with reference to FIG. 1 and FIG. 4, the electronic circuit board 140 and the electronic circuits 150 of the ultrasound transducer 100 are described. The electronic circuits 150 are connected to the side surface of the wiring board block 130 through the electronic circuit board 140. To the electronic circuit board 140, as is the case with the flexible circuit board 120, connection pads are provided on the surface facing the side surface of the wiring board block 130 (reverse surface) and on the surface 141 on the opposite side. The connection pads on the reverse surface (not shown in the figures) are provided according to the arrangement of the second connection pads 133a. These connection pads are connected to the second connection pads 133a.

That is, the connection pads on the reverse surface are conducted with the terminals 110c of the ultrasound vibrators 110a through the second connection pads 133a, the connecting leads 132a, the first connection pads 131a, etc.

Moreover, the connection pads on the reverse surface are, as is the case with the flexible circuit board 120, pulled out to the surface 141 of the electronic circuit board 140 by the penetrating electrodes that penetrate the electronic circuit board 140 (not shown in the figures). Furthermore, the penetrating electrodes that are pulled out up to the surface 141 are connected to the electronic circuits 150 that are disposed on the surface 141 (FIG. 1 and FIG. 2). In this way, the electronic circuits 150 are conducted with the terminals 110c of the ultrasound vibrators 110a by passing through the electronic circuit board 140, the second connection pads 133a, the connecting leads 132a, and the first connection pads 131a.

(The Connection to the Ultrasound Imaging Apparatus Body, Etc.)

Next, the connection between the ultrasound transducer 100 and the ultrasound imaging apparatus body 500 is described with reference to FIG. 6.

Figure 6:
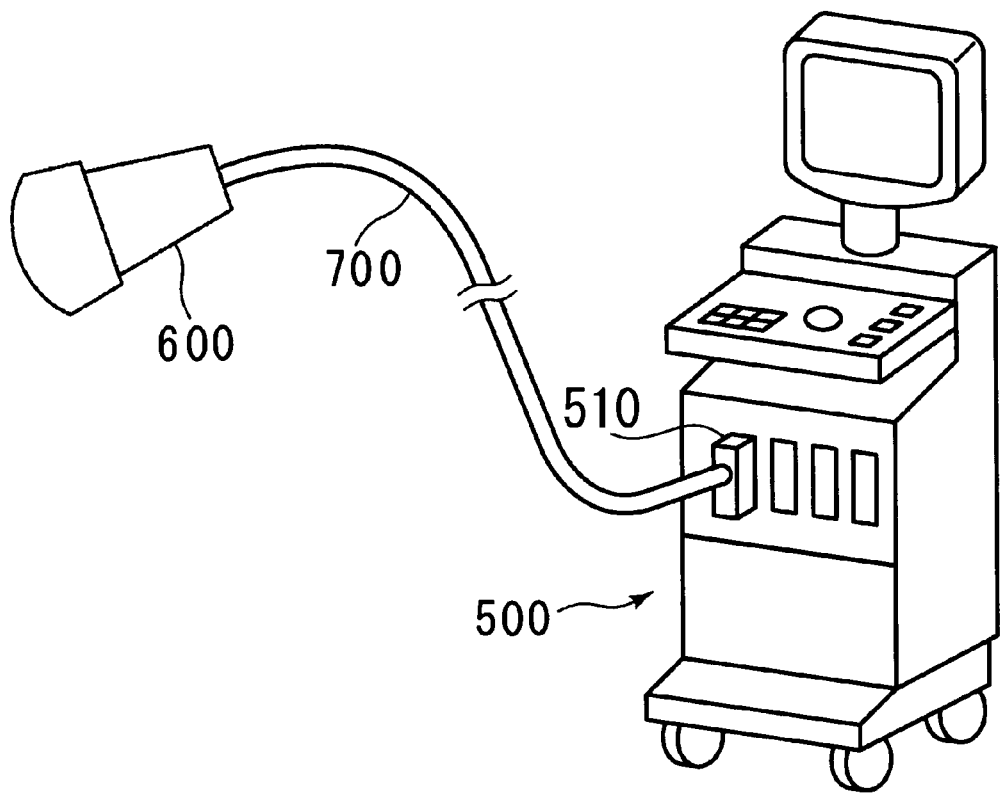
FIG. 6 is a schematic perspective view showing an ultrasound probe including an ultrasound transducer according to the first embodiment, and an ultrasound imaging apparatus.

As shown in FIG. 6, an ultrasound probe 600 contains the ultrasound transducer 100, a cable 700, a relay part (not shown in the figures), etc. The cable 700 connects the ultrasound imaging apparatus body 500 to the ultrasound probe 600. Moreover, the ultrasound imaging apparatus body 500 is connected to the ultrasound transducer 100 through the electronic circuits 150, the relay part, the cable 700, etc. The relay part includes, for example, the electronic circuits that transmit the signals between the electronic circuits 150, a connection part to the cable 700, etc. The cable 700 is the channel for the signals with the ultrasound probe 600. Moreover, it is conducted with the electronic circuits 150 through the connection part of the relay part.

Moreover, the cable 700 is connected to the ultrasound imaging apparatus body 500 through the connector 510.

<Action>

Next, the flow of the signals that are transmitted and received between the ultrasound probe 600 and the ultrasound imaging apparatus body 500, and the action of the ultrasound probe 600 are described.

The transmitter of the ultrasound imaging apparatus body 500 has a voltage circuit and a pulsar circuit. The pulsar circuit repeatedly generates a rate pulse with a predefined rate frequency. This transmitter transmits this rate pulse to the ultrasound probe 600 through the cable 700, the connector 510, etc. Based on the rate pulse, the ultrasound is generated and emitted by each of the ultrasound vibrators 110*a* of the ultrasound transducer 100.

The relay part and the electronic circuits 150 receive the signals that are transmitted by the ultrasound imaging apparatus body 500.

These signals contain the rate pulse. The relay part and the electronic circuits 150 are connected to the group of ultrasound vibrators 110 through the electronic circuit board 140, the wiring board block 130, and the flexible circuit board 120. The signals that the ultrasound probe 600 receives from the ultrasound imaging apparatus body 500 through the relay part and the electronic circuits 150 are transmitted to the terminals 110*c* through the electronic circuit 140, the wiring boards 130*a*, and the flexible circuit board 120. Furthermore, from the terminals 110*c* to the front electrodes or the back electrode of the ultrasound vibrators 110*a*, the voltage that is based on the rate pulse is applied. The piezoelectric transducer is driven by the voltage and emits the ultrasonic pulse. The ultrasonic pulse is transmitted to the subject through the acoustic matching layers and the acoustic lens (not shown in the figures). In this way, the relay part of the ultrasound probe 600 and the electronic circuits 150 cause the ultrasound transducer 100 to transmit the ultrasonic beam.

Subsequently, the ultrasound transducer 100 receives the reflected waves from the subject. The piezoelectric transducer is excited by the reflected waves. When the piezoelectric transducer is excited, the reflected waves are converted to the signals. Each of the converted signals is transmitted to the corresponding electronic circuits 150. With regard to the signals that are transmitted to the electronic circuits 150, an addition processing is performed and the number of channels is reduced by the electronic circuits 150. The signals that are processed in this way are transmitted to the ultrasound imaging apparatus body 500 through the relay part, the cable 700, etc.

The receiving part of the ultrasound imaging apparatus body 500 receives the signals that are processed by the electronic circuits 150 etc., and that is based on the reflected waves from the subject.

Furthermore, the receiving part temporarily stores the processed signals in a memory after amplifying the signals and performing a digital conversion processing. Furthermore, the receiving part provides a focusing delay time for focusing the ultrasonic reflected waves from a predefined depth and a deflecting delay time for deflect for scanning by sequentially changing the reception directionality of the ultrasonic reflected waves. Furthermore, for the output on which this type of beam-forming has been performed, a phasing and adding is performed.

The phasing and adding is a process of, for example, adjusting the phases of the received signals that are obtained from a predefined direction and then adding the signals.

Furthermore, the ultrasound imaging apparatus body 500 generates ultrasonic image data that can be displayed by performing a B-mode signal processing on the received signals. Moreover, by performing a Doppler signal processing, based on the blood flow information, it generates an image of the average blood flow velocity, a distributed image, a power Doppler image, or images resulting from a combination of some of these images.

(The Method for Manufacturing Ultrasound Transducer)

Next, with reference to FIG. 1 to FIG. 5, one example of the manufacturing method of the ultrasound transducer 100 is described.

Specifically, a manufacturing process of the wiring board block 130, and assembly processes of the wiring board block 130, the group of ultrasound vibrators 110, and the electronic circuits 150 are primarily described.

<<Wiring boards>>

A manufacturing process of the wiring boards 130*a* in the manufacturing process of the ultrasound transducer 100 is described with reference to FIG. 2 to FIG. 5. In forming the wiring board block 130, wiring boards 130 are formed. That is, a thick-plate shaped wiring boards 130*a* containing the first board surface 134, the second board surface 132, the side surface 133, the front surface 131, and the rear surface are formed. Here, as shown in FIG. 5, the front surface 131 is formed so as not to be parallel to the rear surface; however, so as to have the curved surface or the sloped-surface. Moreover, the degree of the curvature or the slope of the front surface 131 is, as shown in FIG. 2 to FIG. 4, configured according to the shape of the rear surface of the group of ultrasound vibrators 110. That is, the wiring boards 130*a* are formed such that when the wiring boards 130*a* are laminated in order to form the wiring board block 130, the surface of the wiring board block 130 facing the rear surface of the group of ultrasound vibrators 110 fits the rear surface.

Furthermore, among the wiring boards 130*a*, the wiring board 130*a* that is positioned in the middle of the wiring board block 130 is formed so as to be the highest. Moreover, as shown in FIG. 4, the wiring boards 130*a* are formed such that the height is gradually lowered as it moves toward both ends of the arrangement from the middle.

Moreover, as shown in FIG. 5, for each of the wiring boards 130*a*, the first connection pads 131*a* are provided with a predefined interval. This arrangement interval is, for example, the same as the arrangement interval of the ultrasound vibrators 110*a*. However, the arrangement interval of the first connection pads 131*a* may be wider than the arrangement interval of the ultrasound vibrators 110*a*.

Moreover, the first connection pads 131*a* may not have to be arranged in one row or disposed in the middle of the front surface 131.

For example, depending on the thickness of the wiring boards 130*a*, the first connection pads 131*a* may be arranged on the front surface 131 in a plurality of rows. Moreover, rather than in the middle of the front surface 131, it is possible to arrange the first connection pads 131*a* in the marginal region of the front surface 131.

Moreover, as shown in FIG. 4 and FIG. 5, on the side surface 133 of the wiring boards 130a, the second connection pads 133a are provided with a predefined arrangement interval. Their arrangement interval is fitted to that of the connection pads on the electronic circuit board 140. It is possible, as shown in FIG. 5 as one example, to make the arrangement interval of the second connection pads 133a wider than the interval of the first connection pads 131a. Moreover, it is also possible, for example, to apply arrangement in which groups of the second connection pads 133a are unevenly distribute on the front side or the rear side of the ultrasound transducer 100. Moreover, it is also possible to lean the arrangement of the second connection pads 133a not toward the center of the side surface 133, however, toward the marginal region of the side surface 133. It is also possible to arrange the second connection pads 133a in the plurality of rows.

Moreover, as shown in FIG. 2, FIG. 4, and FIG. 5, the connecting leads 132a are provided to the wiring boards 130a so as to link the first connection pads 131a to the second connection pads 133a. That is, the connecting leads 132a are provided from the first connection pads 131a on the front surface 131, through the second board surface 132, to the second connection pads 133a on the side surface 133. It is possible to form the connecting leads 132a, for example, as a wiring pattern.

Moreover, the disposition interval of the connecting leads 132a in the second board surface 132, for example, as shown in FIG. 5, is the same as the disposition interval of the first connection pads 131a up to the middle of the second board surface 132. Subsequently, the interval of the connecting leads 132a becomes wider according to the disposition interval of the second connection pads 133a.

<<Wiring board block>>

Next, with reference to FIG. 2, FIG. 4, and FIG. 5, a manufacturing process of the wiring board block 130 in the manufacturing process of the ultrasound transducer 100 is described.

The wiring board block 130 is, as shown in FIG. 4 and FIG. 5, formed by placing the plurality of wiring boards 130a, combining them by placing them adjacent to each other, and forming an aggregation of the wiring boards 130a.

As shown in FIG. 5, each of the wiring boards 130a are arranged such that the surfaces on which the first connection pads 131a are provided (front surface 131) facing the same direction. Moreover, the arrangement direction of the wiring boards 130a, for example, is caused to correspond to the arrangement direction of the ultrasound vibrators 110a. Moreover, the heights of the wiring boards 130a are not the same. Among those, the wiring board 130a that is formed so as to be the highest is disposed in the middle of the arrangement. Moreover, as shown in FIG. 4, the wiring boards 130a are arranged such that as it moves toward both ends of the arrangement from the middle, the height gradually decreases. In this way, the wiring board block 130 is formed such that a group of the front surfaces 131 forms a curved surface or a convex surface.

<<Connecting the Group of Ultrasound Vibrators to the Flexible Circuit Board/FIG. 1>>

Next, a process of connecting the group of ultrasound vibrators 110 and the flexible circuit board 120 in the manufacturing process of the ultrasound transducer 100 is described. First, on the assumption of forming the group of ultrasound vibrators 110, layers constituting the ultrasound vibrators 110a are laminated, and a laminated body, which is now shown in the figures, is formed. Each layer referred herein is a block of acoustic matching layer materials, which is not shown in the figures, a block of piezoelectric materials, etc. On the surface on one side of the laminated body in the lamination direction, the terminals 110c are provided with a predefined pitch. This pitch is set so as to fit the arrangement pitch of the ultrasound vibrators 110a in the ultrasound transducer 100.

This laminated body is connected to the flexible circuit board 120. On the surface of the flexible circuit board 120 connected to the laminated body, the third connection pads 121 are provided with a predefined pitch. The pitch for the third connection pads 121 is set so as to fit the arrangement pitch of the terminals 110c. Therefore, when the laminated body and the flexible circuit board 120 are connected to each other, the terminals 110c and the third connection pads 121 are electrically connected.

Furthermore, the laminated body that is connected to the flexible circuit board 120 is divided along the first direction that is perpendicular to the lamination direction. Furthermore, the laminated body is divided along the second direction that is perpendicular to the lamination direction and the first direction. As a result, an element group in which the ultrasound vibrators 110a are two-dimensionally arranged as shown in FIG. 2 is formed.

<<Connecting the Wiring Board Block to the Group of Ultrasound Vibrators>>

As shown in FIG. 2, to the wiring board block 130, the group of ultrasound vibrators 110 that is connected to the flexible circuit board 120 is connected. The wiring board block 130 is formed such that one surface has a desired curved surface or a convex surface. As shown in FIG. 2, according to this surface (front surface), the group of ultrasound vibrators 110 and the flexible circuit board 120 are integrally bent. Furthermore, in this state, through the flexible circuit board 120, the group of ultrasound vibrators 110 is connected to the wiring board block 130.

<<Connection of Electronic Circuit Board>>

Next, with reference to FIG. 2, a process for connecting the electronic circuit board 140 and the electronic circuits 150 to the wiring board block 130 in one example of the manufacturing method of the ultrasound transducer 100 is described. For the electronic circuit board 140, connection pads are provided on the surface facing the side surface of the wiring board block 130 (reverse surface) and on the surface 141 on the opposite side thereof. The electronic circuits 150 are disposed on the connection pads on the surface 141. The electronic circuits 150 are electrically connected to the connection pads on the reverse surface (not shown in the figures) through the connection pads on the surface 141.

As shown in FIG. 1 and FIG. 2, to the side surface 133 of the wiring board block 130, the electronic circuits 150 that are connected to the electronic circuit board 140 are connected. The connection pads on the reverse surface are provided according to the arrangement of the second connection pads 133a. Therefore, the electronic circuits 150 are electrically connected to the terminals 110c of the ultrasound vibrators 110a through the electronic circuit board 140, the second connection pads 133a, the connecting leads 132a, and the first connection pads 131a.

(Action/Effect)

Actions and effects of the ultrasound transducer 100 and the ultrasound probe 600 are described.

As described above, in the ultrasound transducer 100, the wiring board block 130 is provided on the rear surface side of the group of ultrasound vibrators 110. The wiring board block 130 is configured by arranging the plurality of thick-plate shaped wiring boards 130a. For this wiring board block 130, one surface (front surface) has a shape that corresponds to the shape of the rear surface of the group of ultrasound vibrators 110. Furthermore, on this front surface, the first connection pads 131a are provided. The first connection pads 131a are conducted with the terminals 110c of the ultrasound vibrators 110a.

Moreover, the connecting leads 132a are connected to the first connection pads 131a. Furthermore, the connecting leads 132a are connected to the second connection pads 133a that are provided on the side surface of the wiring board block 130 through the second board surface 132. The side surface of the wiring board block 130 has a substantially planiform surface in which the planiform wiring boards 130a are integrated into one string. Furthermore, on the side surface, the electronic circuits 150 are disposed through the electronic circuit board 140. The electronic circuits 150 are conducted with the second connection pads 133a. The electronic circuits 150 transmit and receive the signals between the ultrasound vibrators 110a.

Therefore, with regard to the wiring board block 130, because the surface on which the electronic circuits 150 are disposed is the side surface having a substantially planiform shape, even when the group of ultrasound vibrators 110 is curved or convex, the electronic circuits 150 are easily disposed. Moreover, on the side surface of the wiring board block 130, the connecting leads 132a that are pulled out from each of the ultrasound vibrators 110a are aggregated. Therefore, the connection of the electronic circuits 150 and the relay part, etc. is easily performed. In addition, the wiring of the connecting leads 132a is also easily performed. As a result, regardless of the number and the arrangement pattern of the ultrasound vibrators 110a in the ultrasound transducer 100, the ultrasound transducer 100 with two-dimensional arrangement is easily obtained.

Furthermore, in order to reduce the number of channels from the ultrasound vibrators 110a, it is no longer necessary to mount the electronic circuits 150 directly to the group of ultrasound vibrators 110. As a result, it is no longer necessary to develop a dedicated IC (ASIC) for each specification of the ultrasound transducer. Moreover, the scale (area, etc.) of one of the electric circuits can be oppressed.

Furthermore, using the plurality of IC's, it is possible to perform processing to all elements of the ultrasound transducer 100.

Therefore, the development cost, or manufacturing cost, product cost, etc., of the ultrasound transducer is reduced.

Moreover, the ultrasound vibrators 110a is connected to the wiring board block 130 through the flexible circuit board 120.

Therefore, the flexible circuit board 120 is bent according to the shape/undulation of the rear surface of the group of ultrasound vibrators 110. Furthermore, the flexible circuit board 120 is bent according to the shape/undulation of the front surface of the wiring board block 130. As a result, the terminals 110c of the group of ultrasound vibrators 110 are easily connected to the first connection pads 131a of the wiring board block 130.

[Second Embodiment]

Next, an ultrasound transducer 200 and the ultrasound probe 600 to which the ultrasound transducer 200 is provided according to the second embodiment are described with reference to FIG. 7 to FIG. 11.

Figure 7:
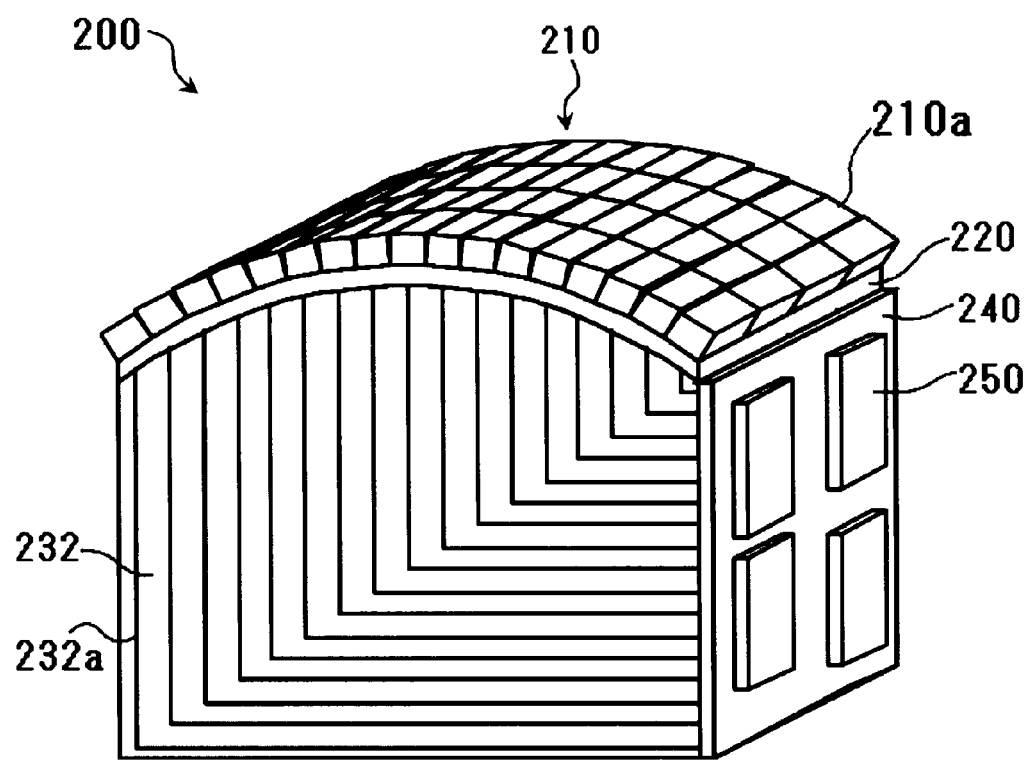
FIG. 7 a schematic perspective view showing an ultrasound transducer according to the second embodiment.
Figure 8:
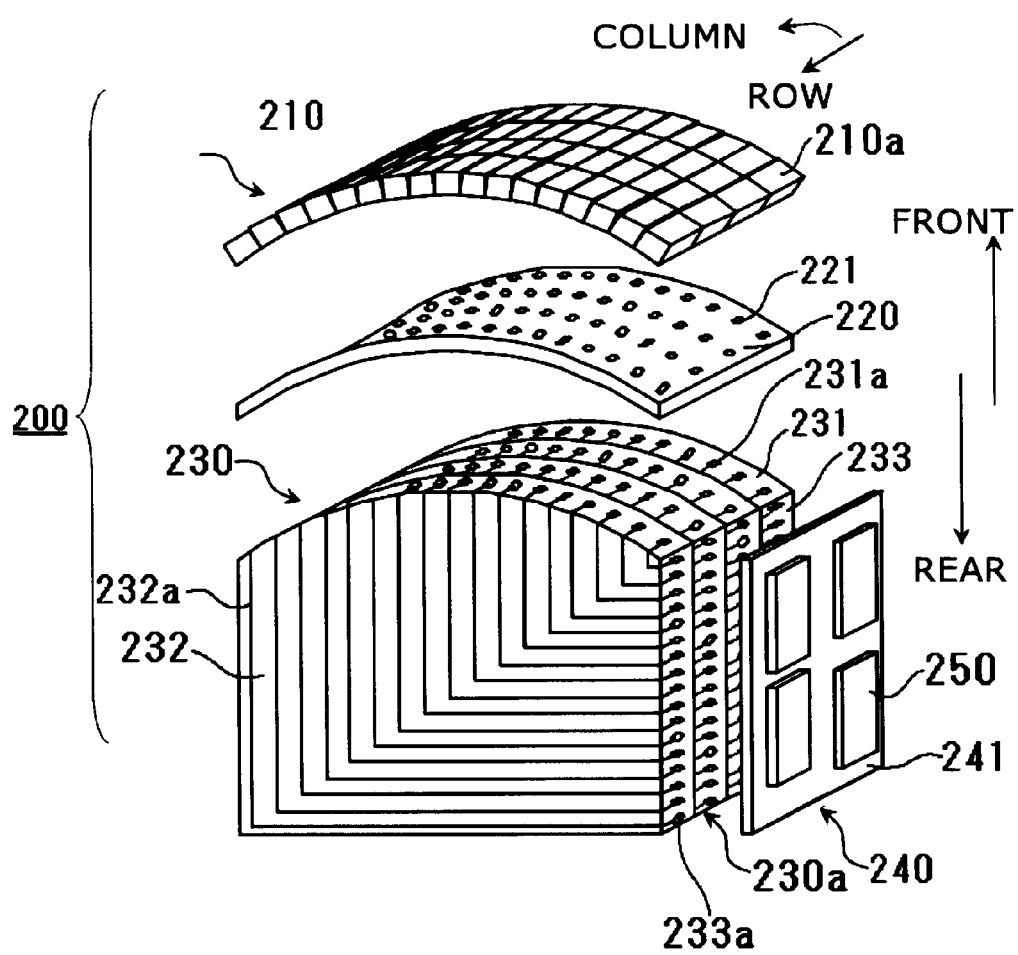
FIG. 8 is a schematic deal perspective view showing the ultrasound transducer according to the second embodiment.
Figure 9:
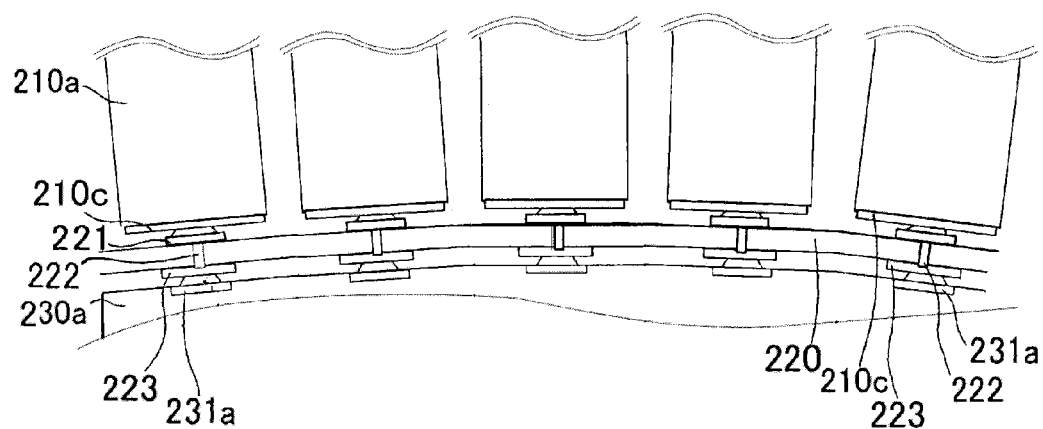
FIG. 9 is, in the ultrasound transducer according to the second embodiment, a schematic cross-sectional view showing a connection state of ultrasound vibrators and wiring boards that are mediated by a flexible circuit board.
Figure 10:
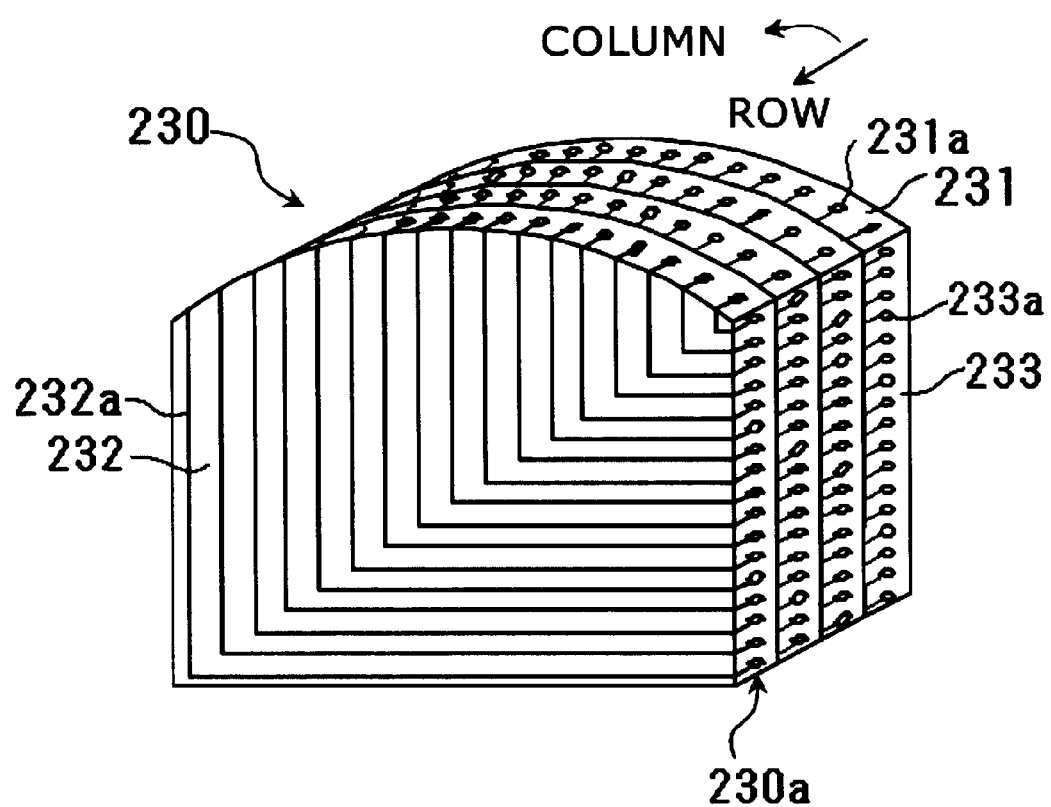
FIG. 10 is a schematic perspective view showing a wiring board block of the ultrasound transducer according to the second embodiment.
Figure 11:
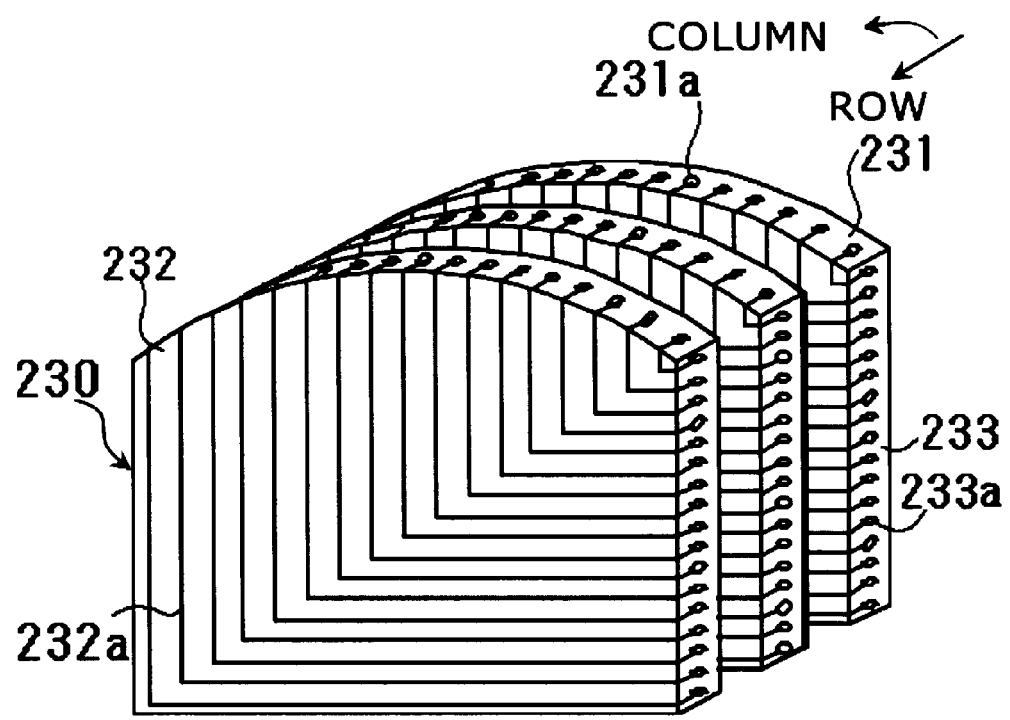
FIG. 11 is a schematic perspective view showing the wiring boards of the ultrasound transducer according to the second embodiment.

FIG. 7 is a schematic perspective view showing the ultrasound transducer 200. FIG. 8 is a schematic deal perspective view showing the ultrasound transducer 200. FIG. 9 is a schematic cross-sectional view showing the connection state of ultrasound vibrators 210a and wiring boards 230a that are mediated by a flexible circuit board 220. FIG. 10 is a schematic perspective view showing a wiring board block 230 of the ultrasound transducer 200. FIG. 11 is a schematic perspective view showing the wiring boards 230a of the ultrasound transducer 200.

Moreover, with regard to the second embodiment, parts that differ from the first embodiment are primarily described. In the second embodiment, explanation for the parts that overlap with the first embodiment may be omitted.

(The Entire Configuration)

As shown in FIG. 7 and FIG. 8, the ultrasound transducer 200 also has a group of ultrasound vibrators 210 that is configured by two-dimensionally arranging the ultrasound vibrators 210a. Moreover, it is possible to configure such that the entire shape of the group of ultrasound vibrators 210 is convex shaped or arc shaped.

Moreover, as shown in FIG. 7 and FIG. 8, on the rear side of the group of ultrasound vibrators 210, the flexible circuit board 220 is disposed adjacently. Moreover, on the rear side of the flexible circuit board 220, the wiring board block 230 configured by arranging the wiring boards 230a having a thick-plate shape is disposed.

Moreover, on the side surface of the wiring board block 230, an electronic circuit board 240 is provided. Moreover, for the wiring board block 230 according to the second embodiment, as is the case with the first embodiment, a side surface having a substantially planiform shape is formed by combining the wiring boards 230a. The side surface of the wiring board block 230 is configured by arranging the side surfaces 233 of wiring boards 230a. On the side surface of the wiring board block 230, the electronic circuit board 240 is provided.

On the surface 241 of this electronic circuit board 240, electronic circuits 250 are provided.

As shown in FIG. 8 and FIG. 9, each of the ultrasound vibrators 210a is connected to the flexible circuit board 220 that is disposed on the rear side. That is, the terminals 210c of the ultrasound vibrators 210a are connected to third connection pads 221 on the flexible circuit board 220. As a result, the ultrasound vibrators 210a are conducted with the flexible circuit board 220 through the terminals 210c and the third connection pads 221. These third connection pads 221 shown in FIG. 8 are conducted with fourth connection pads 223 (refer to FIG. 9) that are provided on the rear surface of the flexible circuit board 220.

That is, the third connection pads 221 are connected to penetrating electrodes 222 (refer to FIG. 9) that are provided for the flexible circuit board 220. Furthermore, the penetrating electrodes 222 are connected to the fourth connection pads 223 on the rear surface of the flexible circuit board 220. As shown in FIG. 9, the fourth connection pads 223 are provided on the rear surface of the flexible circuit board 220, and first connection pads 231a are provided on the front surface 231 of each wiring board 230a. By connecting the rear surface of the flexible circuit board 220 to the front surface of the wiring board block 230, the fourth connection pads 223 are connected to the first connection pads 231a and conductivity is established between them. Moreover, to the first connection pads 231a, connecting leads 232a which pass through a second board surface 232 and the side surface 233 are connected. The connecting leads 232a are provided from the first connection pads 231a, after passing through the second board surfaces 232 of the wiring boards 230a, up to second connection pads 233a. Therefore, conductivity is established between the first connection pads 231a and the second connection pads 233a by the connecting leads 232a.

The front surface of each of the wiring boards 230a and the front surface of the wiring board block 230 are one example of a "first surface", and their rear surfaces are one example of a "second surface".

Moreover, the side surface 233 is one example of a "third surface". Moreover, among the first board surface and the second board surface 232, at least one of them is one example of a "fourth surface".

Moreover, the first connection pads 231a are one example of a "first connection". Moreover, the second connection pads 233a are one example of "second connections". Moreover, the third connection pads 221 are one example of "third connections". Moreover, the fourth connection pads are one example of "fourth connections". Moreover, the fifth connection pads are one example of "fifth connections".

(Wiring Board Block and Wiring Board)

Next, with reference to FIG. 7, FIG. 10, and FIG. 11, the wiring board block 230 and the wiring boards 230a of the ultrasound transducer 200 are described. Moreover, the number of the first connection pads 231a and the number of the wiring boards 230a shown in each figure are shown for conceptual purposes, and they differ from the actual ones. Moreover, the number of the first connection pads 231a provided according to the terminals 210c is also one example, and it is also possible to have other configuration.

The wiring board block 230 establishes wiring between the electronic circuits 250 and the ultrasound vibrators 210a. As shown in FIG. 10, with regard to the ultrasound transducer 200, by disposing the plurality of wiring boards 230a with the same shape and by laminating them adjacent to each other, an aggregate is formed. The aggregate of the wiring boards 230a is the wiring board block 230. With regard to the wiring board block 230, the wiring boards 230a are arranged with the front surface 231 facing the same direction. Moreover, as shown in FIG. 10 and FIG. 11, each of the front surfaces 231 of the wiring boards 230a has the curved surface or convex surface formed according to the shape of the rear surface of the group of ultrasound vibrators 210.

Therefore, the front surface of the wiring board block 230, that is, the aggregate of the front surfaces 231 of the wiring boards 230a also has the curved surface or convex surface according to the entire shape of the rear surface of the group of ultrasound vibrators 210.

Moreover, as shown in FIG. 11, each of the wiring boards 230a according to the second embodiment, as is the case with the wiring boards 130a according the first embodiment, have the widest first board surface (not shown in the figures) and the second board surface 232 on the opposite side. Furthermore, each of the wiring boards 230a has the side surface 233 that is substantially perpendicular to the first board surface and the second board surface 232, and the side surface on the opposite side (not shown in the figures). Moreover, the wiring boards 230a have the rear surface that is perpendicular to the second board surface 232 and the side surface 233 (not shown in the figures), and the front surface 231 that is on the opposite side from this rear surface. That is, the wiring boards 230a are formed in a thick-plate shape having the first board surface, the second board surface 232, the side surface 233, the front surface 231, and the rear surface.

However, the heights (the length in a longitudinal direction) of the wiring boards 230a according to the second embodiment are substantially uniform. That is, as shown in FIG. 8, the front surface 231 of the wiring boards 230a is formed in a shape according to the arrangement pattern of the ultrasound vibrators 210a in the part, of the rear surface of the group of ultrasound vibrators 210, to which the front surface 231 faces. For example, as shown in FIG. 8, if the arrangement pattern of the group of ultrasound vibrators 210 is arc shaped, the shape of the front surface 231 of the wiring boards 230a is formed in an arc shape according to the shape of the facing surface (rear surface) of the group of the ultrasound vibrators 210. However, with regard to the two-dimensional arrangement direction of the ultrasound vibrators 210a, there are cases in which for both the first direction and the second direction that are perpendicular to each other, the arrangement pattern of the ultrasound vibrators 210a is curved or convex shaped. In those cases, the wiring board 230a that is positioned in the middle of the arrangement is formed so as to have the highest height. Furthermore, as it moves toward marginal region of the arrangement, the wiring boards 230a are formed such that the height gradually decreases.

Moreover, as shown in FIG. 10 and FIG. 11, the relationship between the width and the height of the wiring boards 230a differs from the example of the wiring boards 130a according to the first embodiment. That is, with regard to the wiring boards 230a, the width is not necessarily longer than the height. For example, the wiring boards 230a shown in FIG. 11 are formed such that the height is longer than the width.

Moreover, because the configuration of the second board surface 232, the connecting leads 232a, the side surface 233, the second connection pads 233a, the electronic circuit board 240, and the electronic circuits 250, and connection pattern of them are similar to the first embodiment, the explanation is omitted.

Moreover, because the manufacturing method of the ultrasound transducer 200 according to the second embodiment is similar to the manufacturing method of the ultrasound transducer 100 according to the first embodiment, the explanation is omitted. However, with regard to the ultrasound transducer 200, in that one example, there are cases in which the size of all the wiring boards 230a is the same. Therefore, the manufacturing process of the wiring board block 230 in the manufacturing method of the ultrasound transducer 200 is simpler.

Furthermore, when all the wiring boards 230a are the same, it is simpler than the manufacturing process of the wiring boards 230a.

(Action/Effect)

Actions and effects of the ultrasound transducer 200 and the ultrasound probe 600 are described.

Even for the ultrasound transducer 200 according to the second embodiment, the electronic circuits 250 can be disposed on a substantially planiform surface. Therefore, even when the group of ultrasound vibrators 210 has the curved shape or convex shape, the electronic circuits 250 are disposed easily. Furthermore, the connecting leads 232a aggregate on the side surface of the wiring board block 230.

Therefore, the electronic circuits 250 are connected easily to the relay part, etc. Furthermore, the wiring of the connecting leads 232a is also easily performed. As a result, regardless of the number and the arrangement pattern of the ultrasound vibrators 210a, it is possible to obtain the ultrasound transducer 200 with two-dimensional arrangement.

Furthermore, because it is not necessary to mount the electronic circuits 250 directly on the group of ultrasound vibrators 210, it is not necessary to develop a dedicated IC (ASIC) for each specification of the ultrasound transducer. Moreover, the scale of one of the electric circuits can be oppressed. Therefore, the development cost, or manufacturing cost, product cost, etc., are reduced.

Moreover, the ultrasound vibrators 210a are connected to the wiring board block 230 through the flexible circuit board 220 that have flexibility. Therefore, the terminals 210c of the group of ultrasound vibrators 210 are easily connected to the first connection pads 231a.

Furthermore, in the second embodiment, it is possible to configure such that the size of all the wiring boards 230a of the wiring board block 230 is the same. Therefore, it is possible to simplify the manufacturing process of the wiring board block 230 and the manufacturing process of the wiring boards 230a.

[Third Embodiment]

Figure 12:
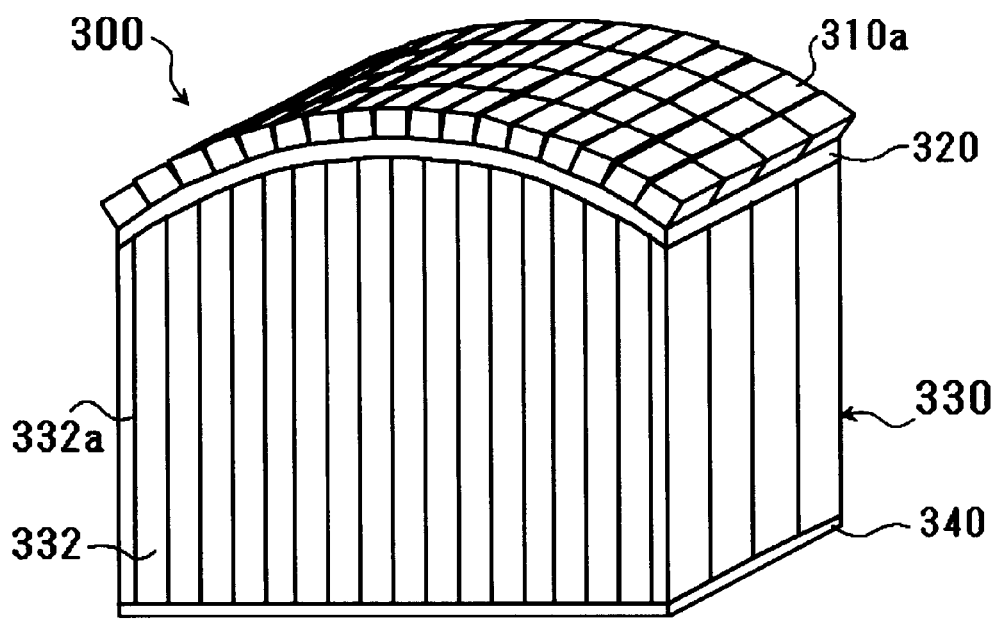
FIG. 12 a schematic perspective view showing an ultrasound transducer according to the third embodiment.
Figure 13:
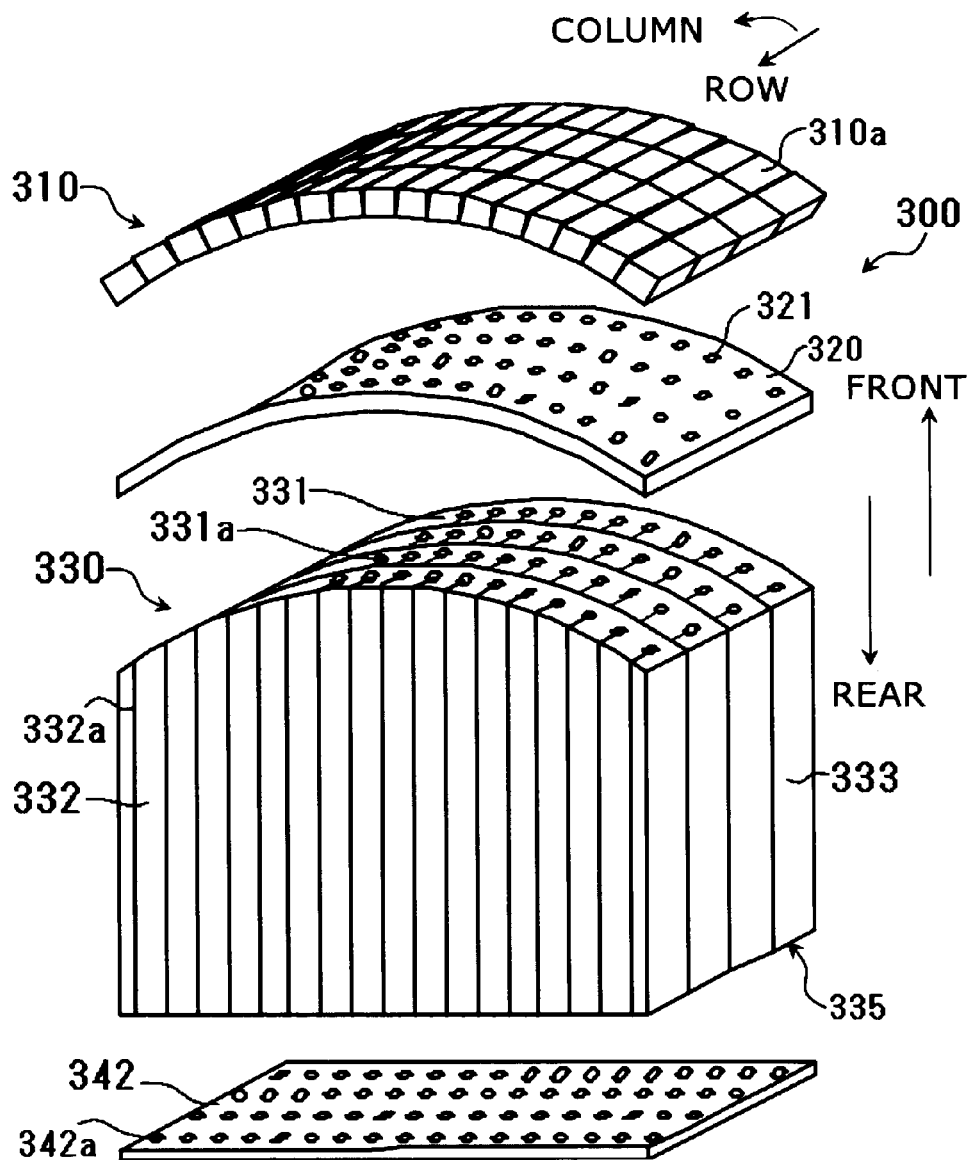
FIG. 13 is a schematic deal perspective view showing the ultrasound transducer according to the third embodiment.
Figure 14:
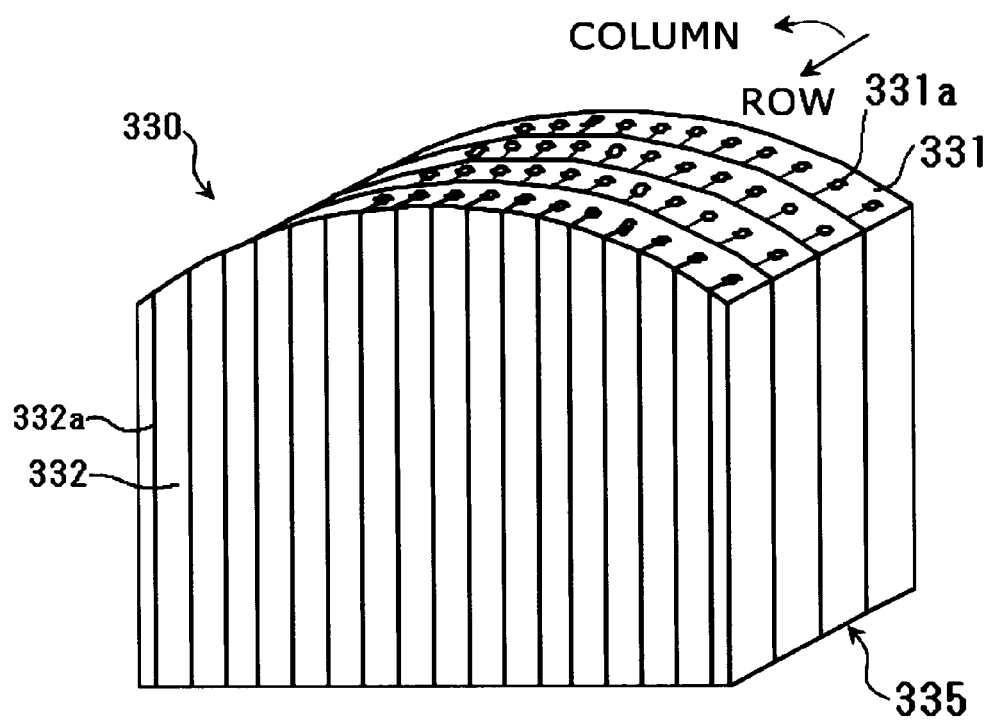
FIG. 14 is a schematic perspective view showing a wiring board block of the ultrasound transducer according to the third embodiment.

Next, an ultrasound transducer 300 according to the third embodiment and the ultrasound probe 600 to which the ultrasound transducer 300 is provided are described with reference to FIG. 12 to FIG. 15. FIG. 12 is a schematic perspective view showing the ultrasound transducer 300. FIG. 13 is a schematic deal perspective view showing the ultrasound transducer 300. FIG. 14 is a schematic perspective view showing a wiring board block 330 of the ultrasound transducer 300.

Figure 15:
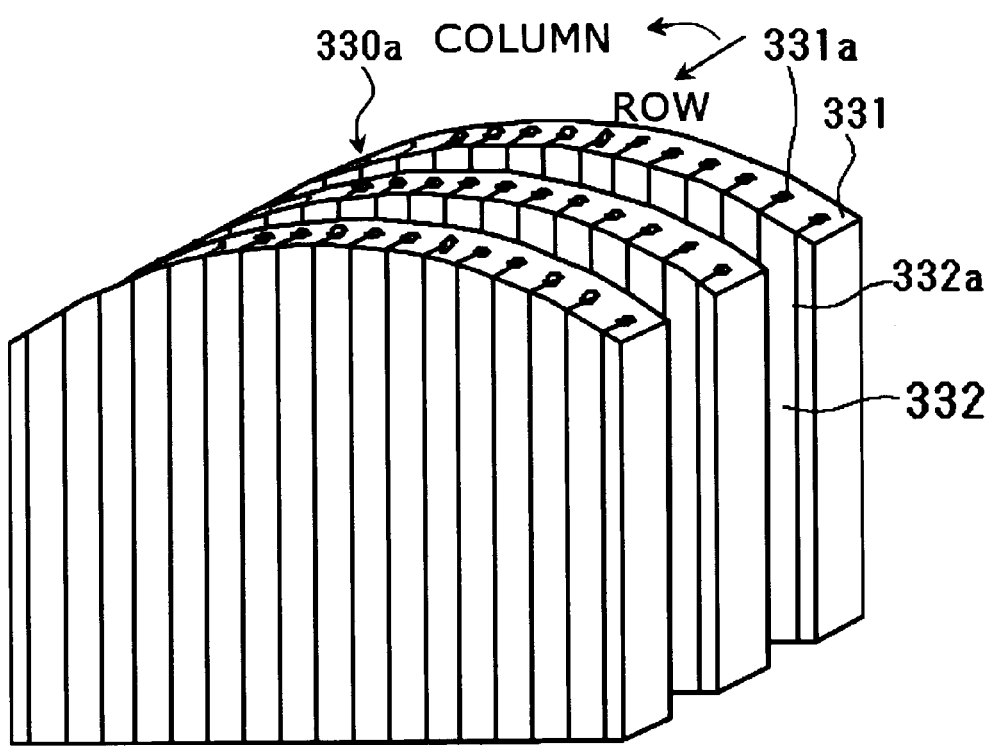
FIG. 15 is a schematic perspective view showing the wiring boards of the ultrasound transducer according to the third embodiment.

FIG. 15 is a schematic perspective view showing wiring boards 330a of the ultrasound transducer 300. Moreover, with regard to the third embodiment, the parts that differ from the first and second embodiments are primarily described. With regard to the third embodiment, explanation regarding the sections that overlaps with the first or second embodiment may be omitted.

(Entire Configuration)

As shown in FIG. 12 and FIG. 13, the ultrasound transducer 300 also has a group of ultrasound vibrators 310 that is configured by two-dimensionally arranging ultrasound vibrators 310a. Moreover, it is possible to configure such that the entire shape of the group of ultrasound vibrators 310 is convex shaped or arc shaped.

Moreover, as shown in FIG. 12 and FIG. 13, as is the case with the first embodiment and the second embodiment, the ultrasound vibrators 310a are connected to the wiring board block 330 through a flexible circuit board 320. As shown in FIG. 14 and FIG. 15, the wiring board block 330 is configured by arranging the wiring boards 330a having a thick-plate shape.

However, as shown in FIG. 12 and FIG. 13, as is different from the first embodiment and the second embodiment, for the wiring board block 330, an electronic circuit board 340 is provided to a group of rear surfaces 335. That is, the wiring board block 330 is configured by laminating the wiring boards 330a. When the wiring boards 330a are laminated, the group of rear surfaces 335 having substantially planiform shape configured by stringing up the rear surfaces is formed.

To the group of rear surfaces 335, the electronic circuit board 340 is provided.

On the group of rear surfaces 335, second connection pads are arranged (not shown in the figures). As shown in FIG. 13, on a reverse surface 342 of the electronic circuit board 340, fifth connection pads 342a corresponding to the second connection pads of the wiring board block 330 are provided. Moreover, on the surface, which is not shown in the figures, of the electronic circuit board 340, electronic circuits (not shown in the figures) are provided.

Moreover, because the connection configuration of the ultrasound vibrators 310a, the flexible circuit board 320, and the front surface 331 of the wiring board block 330 is similar to the first embodiment and the second embodiment, an explanation is omitted.

(Wiring Board Block and Wiring Boards)

Next, with reference to FIG. 12, FIG. 14, and FIG. 15, the wiring board block 330 and the wiring boards 330a of the ultrasound transducer 300 are described. Moreover, the number of the first connection pads 331a and the number of the wiring boards 330a of the wiring board block 330 shown in each figure are shown for conceptual purposes, and they differ from the actual ones. Moreover, the number of the first connection pads 331a according to the terminals (not shown in the figures) on the rear surface of the ultrasound vibrators 310a is also one example, and it is also possible to have other configuration.

As shown in FIG. 14, the wiring board block 330 is an aggregate that is formed by disposing the plurality of wiring boards 330a and by laminating them by placing them adjacent to each other. This aggregate becomes the wiring board block 330. The front surface 331 of the wiring board block 330, as is the case with the second embodiment, has a curved or convex shape configured according to the shape of the rear surface of the group of ultrasound vibrators 310. With regard to the wiring board block 330, as shown in FIG. 14 and FIG. 15, the front surfaces 331 of the wiring boards 330a are combined so as to face the same direction.

Moreover, as shown in FIG. 14, each of the wiring boards 330a according to the third embodiment, as is the case with the wiring boards 130a according to the first embodiment, has the widest first board surface (not shown in the figures) and the second board surface 332 on the opposite side. Furthermore, it has the side surface 333 that is substantially perpendicular to the first board surface and the second board surface 332, and the side surface on the opposite side (not shown in the figures). Moreover, each of the wiring boards 330a has the rear surface that is perpendicular to the second board surface 332 and the side surface 333, and the front surface 331 that is on the opposite side from this rear surface. That is, each of the wiring boards 330a is formed in a thick-plate shape having the first board surface, the second board surface 332, the side surface 333, the front surface 331, and the rear surface.

Moreover, as shown in FIG. 15, the height (the length in the longitudinal direction) of the wiring boards 330a, as is the case with the second embodiment, is almost uniform. Moreover, as is the case with the second embodiment, the front surface 331 of the wiring boards 330a is also formed according to the shape of the part in which the front surface 331 faces the group of ultrasound vibrators 310.

Moreover, as is the case with the second embodiment, with regard to the two-dimensional arrangement of the ultrasound vibrators 310a, there are cases in which both the first direction and the second direction perpendicular to each other in the arrangement are curved or convex shaped. In those cases, the wiring board 330a that is positioned in the middle of the arrangement is formed so as to have the highest height. Furthermore, as it moves toward marginal parts of the arrangement, it is formed such that the height of the wiring boards 330a gradually decreases. The relationship between the width and the height of each of the wiring boards 330a is the same as the wiring boards 230a according to the second embodiment.

Here, with regard to the wiring board block 330 according to the third embodiment, the configuration of and the connection relationship with one another between the second board surface 332, connecting leads 332a, the side surface 333, the second connection pads (not shown in the figures), the electronic circuit board 340, and the electronic circuits differ from the first and second embodiments. These configurations are described below.

As shown in FIG. 13 to FIG. 15, for the wiring boards 330a, the second connection pads are not provided on the side surface 333. These second connection pads are arranged on the group of rear surfaces 335 of the wiring board block 330. That is, on the rear surface of the wiring boards 330a, the second connection pads (not shown in the figures) are provided with almost the same arrangement interval as the first connection pads 331a. Therefore, the connecting leads 332a are pulled out from the first connection pads 331a to the second board surface 332 in substantially linear shape. Furthermore, the connecting leads 332a run toward the rear surface of the wiring boards 330a.

Furthermore, the connecting leads 332a are connected to the second connection pads that are arranged on the rear surface of the wiring boards 330a.

Furthermore, as shown in FIG. 13, the electronic circuit board 340 is connected to the rear surface of the wiring board block 330. As a result, the second connection pads that are arranged on the group of rear surfaces 335 are connected to the fifth connection pads 342a that are arranged on the reverse surface 342 of the electronic circuit board 340. Furthermore, the second connection pads are conducted with the electronic circuits on the surface of the electronic circuit board 340.

With regard to the connection configuration of the second connection pads and the electronic circuits that are mediated by the electronic circuit board 340, because it is the same as the first embodiment and the second embodiment, an explanation is omitted.

Moreover, the wiring boards 330a are not limited to the configuration shown in FIG. 14 and FIG. 15, and for example, they may have a configuration similar to the wiring boards 130a according to the first embodiment.

The front surfaces of the wiring boards 330a and the front surface of the wiring board block 330 are one example of a "first surface". Moreover, the rear surface is one example of a "second surface". Moreover, the first connection pads 331 a are one example of "first connection". Moreover, the second connection pads are one example of "second connections". Moreover, the third connection pads 321 are one example of "third connections". Moreover, the fourth connection pads 223 are one example of "fourth connections".

Moreover, the fifth connection pads 342a are one example of "fifth connections".

(Action/Effect)

Actions and effects of the ultrasound transducer 300 and the ultrasound probe 600 are described.

Even for the ultrasound transducer 300, the electronic circuits can be disposed on a substantially planiform surface. Therefore, even when the group of ultrasound vibrators 310 has the curved shape or convex shape, the electronic circuits can be disposed easily.

Furthermore, the connecting leads 332a aggregate on the group of rear surfaces 335 of the wiring board block 330. Therefore, the electronic circuits are connected easily to the relay part, etc.

Furthermore, the wiring of the connecting leads 332a is also easily performed. As a result, regardless of the number and the arrangement pattern of the ultrasound vibrators 310a, it is possible to obtain the ultrasound transducer 300 with two-dimensional arrangement.

Furthermore, because it is not necessary to mount the electronic circuits directly on the group of ultrasound vibrators 310, it is not necessary to develop a dedicated IC (ASIC) for each specification of the ultrasound transducer. Moreover, the scale of one of the electric circuits can be oppressed. Therefore, the development cost, or manufacturing cost, product cost, etc., are reduced.

Moreover, the ultrasound vibrators 310a and the wiring board block 330 are connected through the flexible circuit board 320 that have flexibility. Therefore, the terminals of the group of ultrasound vibrators 310 are easily connected to the first connection pads 331a.

Furthermore, in the third embodiment, it is possible to configure such that the size of all the wiring boards 330a is the same. Therefore, it is possible to simplify the manufacturing process of the wiring boards block 330 and the manufacturing process of the wiring boards 330a.

[Modified Example]

Next, a modified example of the ultrasound transducer according to the above first embodiment to the third embodiment is described with reference to FIG. 16A and FIG. 16B.

Figure 16A:
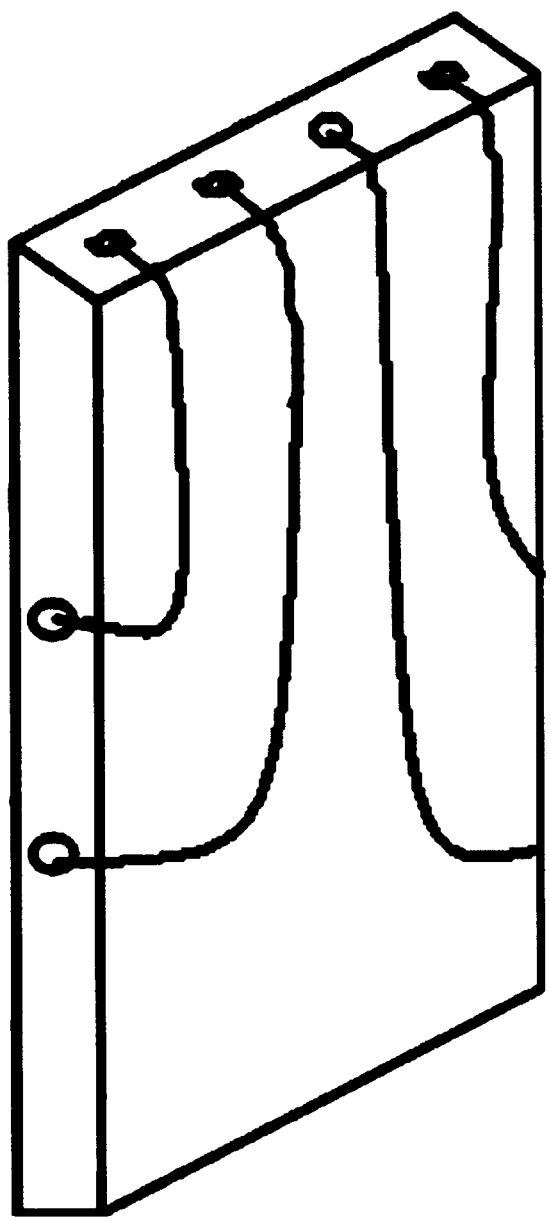
FIG. 16A is a schematic perspective view showing the wiring boards of the ultrasound transducer according to a modification of the first embodiment.

FIG. 16A is a schematic perspective view showing the wiring boards of the ultrasound transducer according to the modified example of the first embodiment.

Figure 16B:
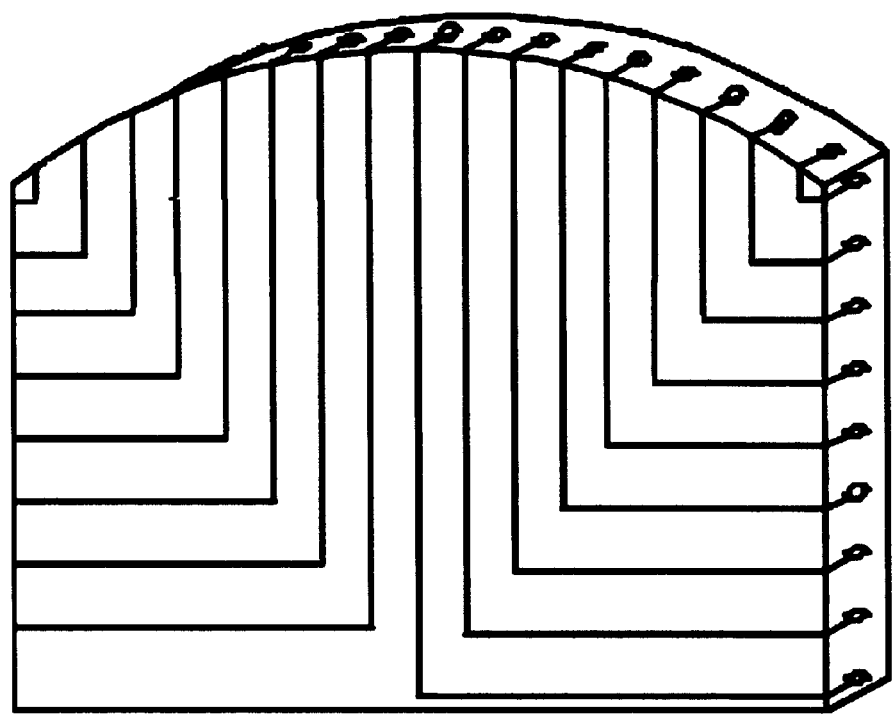
FIG. 16B is a schematic perspective view showing the wiring boards of the ultrasound transducer according to a modification of the second and third embodiments.

FIG. 16B is a schematic perspective view showing the wiring boards of the ultrasound transducer according to the modified example of the second embodiment and the third embodiment.

As shown in FIG. 5, FIG. 10, and FIG. 15, with regard to the wiring boards of the ultrasound transducer described above, although the second connection pads are provided on one surface only (the side surface 133, the side surface 233, the group of rear surfaces 335, etc.), they are not limited to this configuration. For example, as shown in FIG. 16A or FIG. 16B, it is possible to arrange the second connection pads on two surfaces, namely on the side surface of the wiring board and on the side surface on the opposite side. Moreover, it is also possible to arrange the second connection pads on two surfaces, namely on the side surface and on the rear surface of the wiring board.

Moreover, it is also possible to provide the second connection pads on three surfaces of the wiring boards. In these cases, the connecting leads 132a that are pulled out from the first connection pads are formed according to the disposition of the second connection pads.

Even for this modified example, as is the case with the ultrasound transducer according to the above first embodiment to the third embodiment, regardless of the number and the arrangement pattern of the ultrasound vibrators, it is possible to obtain ultrasound transducer with the two-dimensional arrangement, and the ultrasound probe containing this ultrasound transducer. Moreover, with regard to the modified example, the connecting leads are pulled out on the plurality of surfaces of the wiring board. Therefore, the wiring of the connecting leads is easily performed. Furthermore, it is possible to provide a margin to the arrangement interval of the second connection pads.

Moreover, the connecting leads are not limited to the configuration in which they are connected to the second connection pads through the second board surface of the wiring boards. For example, it is possible to configure such that the connecting leads are passed through both the second board surface and the first board surface of the wiring boards. In these cases, insulation sheet, etc., are provided between the wiring boards.

Moreover, with regard to the ultrasound transducer according to the above first embodiment to the third embodiment, based on a perspective of adjusting the arrangement with the ultrasound vibrators, for one column (or for one row) in a two-dimensional arrangement of the ultrasound vibrators, one wiring board is allocated. However when it is not difficult to adjust the arrangement, for example, for two columns (or for two rows) of the ultrasound vibrators, it is also possible to allocate one wiring board. That is, for the plurality of columns (or rows) of the ultrasound vibrators, it is also possible to allocate one wiring board.

Moreover, with regard to the ultrasound transducer according to the above first embodiment to the third embodiment, the front surface and the rear surface of the group of ultrasound vibrators may be the curved surface or convex surface. However, by arranging the ultrasound vibrators in a planar shape, the group of ultrasound vibrators may be formed in a planar shape. In these cases, the surface of the wiring boards on the ultrasound vibrator side (that is, the front surface of the wiring boards) is formed not as the sloped surface or the curved surface; however, as the planar surface that is perpendicular to the side surface of the wiring boards. Moreover, in these cases, if it is not difficult to connect the group of ultrasound vibrators to the wiring board block, the flexible circuit board may not have to be provided between them.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound transducer, comprising:
   a group of ultrasound vibrators composed of two-dimensionally arranged ultrasound vibrators, each of which includes a piezoelectric transducer in which a front electrode is formed on a front surface that is an ultrasonic radiation surface and in which a back electrode is formed on a rear surface;
   a wiring board block composed of a laminate, along the row direction or the column direction with respect to the two-dimensional arrangement, and including a plurality of wiring boards, wherein each wiring board has a first surface facing said rear surface of said ultrasound vibrators and a second surface on an opposite side to the first surface;
   first connection parts provided on said first surface corresponding to the arrangement of said ultrasound vibrators and to be conducted with said back electrodes;
   second connection parts provided on a third surface that is perpendicular to said second surface;
   connecting leads configured to establish conductivity between said first connection parts and said second connection parts on a fourth surface that is perpendicular to both the second surface and a third surface of said wiring boards; and
   electronic circuits configured to be connected to a surface of said wiring board block on which said second connection parts are provided, to be conducted with said second connection parts, and to process signals from said piezoelectric transducers,
   wherein a shape of an entire arrangement of said ultrasound vibrators is a curved shape; and
   the first surfaces of said wiring boards which face said rear surfaces of said ultrasound vibrators are formed as a curved shape corresponding to a shape of said rear surfaces, based on the arrangement of said ultrasound vibrators.

2. The ultrasound transducer according to claim 1, wherein said third surface of said wiring boards is wider than said fourth surface.

3. The ultrasound transducer according to claim 2, wherein for said wiring boards, the third surfaces to which said electronic circuits are connected form a flat surface.

4. The ultrasound transducer according to claim 1, wherein each of said first surfaces of said wiring boards is formed in the curved shape corresponding to a curvature of the entire arrangement of said ultrasound vibrators; and
   a facing surface of said wiring board block is formed as a substantially continuous surface of said first surfaces resulting from the arrangement of said wiring boards, and is formed in accordance with the curved surface in the entire arrangement of said ultrasound vibrators.

5. The ultrasound transducer according to claim 1, further comprising:
   a connection board configured to be disposed between said ultrasound vibrators and said wiring board block, to have flexibility, and to establish conductivity between said back electrode of each of said piezoelectric transducers and the corresponding one of said first connection parts.

6. The ultrasound transducer according to claim 5, wherein third connection parts configured to be conducted with said back electrodes are provided on a surface of said connection board that faces said rear surfaces of said ultrasound vibrators, and
   fourth connection parts configured to be conducted with said third connection parts, and to be disposed such that a disposition interval is greater than that of said third connection parts are provided on a surface of said connection board that faces said first surfaces of said wiring boards.

7. The ultrasound transducer according to claim 1, further comprising:
   an electronic circuit board configured to be disposed such that one surface faces said second surface or said third surface of said wiring boards, and to have fifth connection parts that are connected to said second connection parts, respectively, wherein
   said electronic circuits are provided on a surface opposite to said one surface of said electronic circuit board.

8. The ultrasound transducer according to claim 1, wherein said second surface of each wiring board is formed so as to be longer than a length of said front surface; and
   a disposition interval of said second connection parts is equal to or greater than that of said first connection parts.

9. The ultrasound transducer according to claim 4, wherein a length of each first surface of said wiring boards is equal to or greater than a length of one row or one column in the entire arrangement of said ultrasound vibrators; and
   a disposition interval of said first connection parts is equal to or greater than that of said ultrasound vibrators.

10. An ultrasound probe, comprising:
    a group of ultrasound vibrators composed of two-dimensionally arranged ultrasound vibrators, each of which includes a piezoelectric transducer in which a front electrode is formed on a front surface that is an ultrasonic radiation surface and in which a back electrode is formed on a rear surface;
    a wiring board block composed of a laminate, along the row direction or the column direction with respect to the two-dimensional arrangement, and including a plurality of wiring boards, wherein each wiring board has a first surface facing said rear surface of said ultrasound vibrators and a second surface on an opposite side to the first surface;
    first connection parts provided on said first surface corresponding to the arrangement of said ultrasound vibrators and to be conducted with said back electrodes;
    second connection parts provided on a third surface that is perpendicular to said second surface;

connecting leads configured to establish conductivity between said first connection parts and said second connection parts on a fourth surface that is perpendicular to both the second surface and the third surface of said wiring boards; and electronic circuits configured to be connected to a surface of said wiring board block on which said second connection parts are provided, to be conducted with said second connection parts, and to process signals from said piezoelectric transducers; and an interface part configured to establish conductivity between an external device and said electronic circuits, wherein a shape of an entire arrangement of said ultrasound vibrators is a curved shape; and the first surface of said wiring board block which faces said rear surfaces of said ultrasound vibrators is formed as a curved shape corresponding to a shape of said rear surfaces, based on the arrangement of said ultrasound vibrators.

* * * * *